(12) United States Patent
Jessen et al.

(10) Patent No.: US 9,493,793 B2
(45) Date of Patent: Nov. 15, 2016

(54) COMPOSITIONS AND METHODS FOR INCREASED ETHANOL TITER FROM BIOMASS

(75) Inventors: Holly J. Jessen, Chanhassen, MN (US); Jian Yi, Carlsbad, CA (US)

(73) Assignee: Cargill, Incorporated, Wayzata, MN (US)

( * ) Notice: Subject to any disclaimer, the term of this patent is extended or adjusted under 35 U.S.C. 154(b) by 489 days.

(21) Appl. No.: 13/988,899

(22) PCT Filed: Nov. 22, 2011

(86) PCT No.: PCT/US2011/061955
§ 371 (c)(1),
(2), (4) Date: May 22, 2013

(87) PCT Pub. No.: WO2012/071470
PCT Pub. Date: May 31, 2012

(65) Prior Publication Data
US 2013/0252301 A1 Sep. 26, 2013

Related U.S. Application Data

(60) Provisional application No. 61/416,169, filed on Nov. 22, 2010.

(51) Int. Cl.
C12P 7/06 (2006.01)
C12N 9/04 (2006.01)
C12P 7/10 (2006.01)

(52) U.S. Cl.
CPC ............ C12P 7/06 (2013.01); C12N 9/0006 (2013.01); C12P 7/065 (2013.01); C12P 7/10 (2013.01); Y02E 50/16 (2013.01); Y02E 50/17 (2013.01); Y02P 20/52 (2015.11)

(58) Field of Classification Search
None
See application file for complete search history.

(56) References Cited

U.S. PATENT DOCUMENTS

| | | | |
|---|---|---|---|
| 9,090,918 B2 * | 7/2015 | Jessen | C12N 1/18 |
| 2009/0081746 A1 | 3/2009 | Liao et al. | |
| 2009/0226989 A1 | 9/2009 | Suominen et al. | |
| 2010/0291653 A1 | 11/2010 | Ness et al. | |
| 2014/0030730 A1* | 1/2014 | Mueller | C07K 14/33 435/6.18 |

FOREIGN PATENT DOCUMENTS

WO 2006069610 7/2006

OTHER PUBLICATIONS

Suwannarangsee et al., "Characterization of alcohol dehydrogenase 1 of the thermotolerant methylotrophic yeast *Hansenula polymorpha*," Appl Microbiol Biotechnol (2010), pp. 88:497-507, Published online: Jul. 16, 2010.

Yurimoto et al., "Alcohol dehydrogenases that catalyse methyl formate synthesis participate in formaldehyde detoxification in the methylotrophic yeast *Candida boldinii*," Yeast 2004, pp. 21: 341-350, Published online in Wiley InterScience (www.interscience.wiley.com).

Grey et al., "Overexpression of ADH1 confers hyper-resistence to formaldehyde in *Saccharomyces cerevisiae*," Curr Genet (1996), pp. 29:437-440, Springer-Verlag 1996.

Young et al., "Evolution of a glucose-regulated ADH gene in the gene *Saccharomyces*," Gene an International Journal on Genes, Genomes and Evolution, (2000), pp. 299-309, Published online (www.elsevier.com/locate/gene).

Thompson et al., "Resurrecting ancestral alcohol dehydrogenases from yeast," Nature Genetics, Jun. 2005, pp. 630-635, vol. 37; No. 6, Published online: Nature Publishing Group (http://www.nature.com/naturegenetics).

Cho et al., "Transcriptional Control of ADH Genes in the Xylose-Fermenting Yeast *Pitchia stipitis*," Applied and Environmental Microbiology, Jun. 1999, pp. 2263-2368, 1999, American Society for Microbiology.

Gutierrez-Lomeli et al., "Overexpression of ADH1 and HXT1 genes in the yeast *Saccharomyces cerevisiae*improves the fermentative efficiency during tequila elaboration," Springer Science+Business Media B.V., Nov. 7, 2007, pp. 93:363-371, Published online: Feb. 2008.

Denis et al., "mRNA Levels for the Fermentative Alcohol Dehydrogenase of *Saccharomyces cerevisiae*Decrease upon Growth on a Nonfermentable Carbon Source," The Journal of Biological Chemistry, (1983), pp. 1165-1171, vol. 258; No. 2, Issue of Jan. 25.

Lin et al., "The Alcohol Dehydrogenase System in the Xylose-Fermenting Yeast *Candida maltosa*," Plos One, Published online (www.plosone.org), Jul. 2010, pp. 1-9, vol. 5; Issue 7.

Smidt et al., "The alcohol dehydrogenases of *Saccharomyces cerevisiae*: a comprehensive review," 2008 Federation of European Microbiological Societies, May 8, 2008, pp. 967-978, Published online, Blackwell Publishing Ltd.

Maestre et al., "Effects of ADH2 Overexpression in *Saccharomyces bayanus* during Alcoholic Fermentation," Applied and Environmental Microbiology, Feb. 2008, pp. 702-707, American Society for Microbiology, vol. 74; No. 3.

Dhaliwal et al.; "Enhanced ethanol production from sugarcane juice by glactose adaption of a newly isolated thermotolerant strain of Pichia kudriavzevii", Bioresource Technology, vol. 102, Mar. 12, 2011, pp. 5968-5975, XP028407860.

Hisamatsu et al.; "Isolation and identification of a novel yeast fermenting ethanol under acidic conditions", Journal of Applied Glycoscience, vol. 53, 2006, pp. 111-113, XP055230776.

(Continued)

Primary Examiner — Anand Desai

(57) ABSTRACT

The present application discloses the identification of novel *I. orientalis* ADH1, ADHa, and ADHb genes, and the production and characterization of genetically modified yeast cells in which these genes were altered. Provided herein are isolated *I. orientalis* ADH1, ADHa, and ADHb polynucleotides and polypeptides, genetically modified yeast cells that overexpress *I. orientalis* ADH1 and/or contain deletions or disruptions of ADHa and/or ADHb, and methods of using culturing these modified cells to produce ethanol.

12 Claims, 15 Drawing Sheets

(56) References Cited

OTHER PUBLICATIONS

Hughes et al.; "Automated yeast transformation protocol to engineer *Saacharomyces cerevisiae* strains for cellulosic ethanol production with open reading frames that express proteins binding to xylose isomerase identified using a robotic two-hybrid screen", JALA, vol. 14, 2009, pp. 200-212, XP026321487.

Kwon et al.; "Effect of lignocellulosic inhibitory compounds on growth and ethanol fermentation of newly-isolated thermotolerant Issatchenkia orientalls", Bioresource Technology, vol. 102, Jun. 14, 2011, pp. 8099-8104, XP002752792.

Laluce: "Ethanol production from sugarcane bagasse: Enzymatic hydrolysis, microbiological assays to evaluate tolerance of yeasts to the toxicity of hydrolysates and fermentation at high temperatures", Sao Paulo State University, Institute of Chemistry / FAPE SP Bioenergy program Project presentation, Jun. 2010, pp. 34-35, XP002752789, URL:///www.fapesp.br/publicacoes/pastabioen_jun2010.pdf.

Nakayama et al.; "Candida krusei produces ethanol without production of succinic acid; a potential advantage for ethanol recovery by pervaporation membrane separation", FEMS Yeast Research, vol. 8, 2008, pp. 706-714, XP002752788.

Qin et al.; "Biodegradation of xylitol fermentation inhibitors by Issatchenkia orientalis", Guangxi Sciences, vol. 17, Jul. 2010, pp. 358-362, XP002752790.

Sandhu et al.; "Ethanol production from Kinnow madarin (Citrus reticulata) peels via simultaneous saccharification and fermentation using crude enzyme produced by Aspergillus oryzae and the thermotolerant Pichia kudriavzevii strain", Annals of Microbiology, vol. 62, Jul. 8, 2011, pp. 655-666, XP002752793.

Thalagala et al.; "Study on ethanol fermentation using D-glucose rich fractions obtained from lignocelluloses by a two-step extraction with sulfuric acid and Issatchenkia orientalis MF 121", Journal of Applied Glycoscience, vol. 56, 2009, pp. 7-11, XP002750966.

Yao et al.; "Gene cloning, expression, and characterization of a novel acetaldehyde dehydrogenase from Issatchenkia terricola strain XJ-2", Applied Microbiology and Biotechnology, vol. 93, Aug. 20, 2011, pp. 1999-2009, XP002752795.

Zhao et al.; "Research progress on bio-detoxification of lignocellulose hydrolysate", Journal of Guilin University of Technology, vol. 31, Aug. 2011, pp. 443-449, XP002752794.

\* cited by examiner

Figure 15

Sc = *S. cerevisiae*

```
ScADH1   (SEQ ID NO:13)     1 ------------------------------ms--ipetqkgvifyeshgkleykdipvpkp
ScADH2   (SEQ ID NO:14)     1 ------------------------------ms--ipetqkaiifyesngklehkdipvpkp
ScADH3   (SEQ ID NO:15)     1 mlrtstlftrrvqpslfsrnilrlqst--aa--ipktqkgvifyenkgklhykdipvpep
S141G2556 (SEQ ID NO:6)     1 ------------------------------msyeipqtqkacvfyenggpitykdipvpkp
S141G9091 (SEQ ID NO:2)     1 mfastfrsqavraarftrfqst-------fa--ipekqmgvifethggplqykeipvpkp
S141G1202 (SEQ ID NO:4)     1 mlsktitaalrgnttrtafrinairslaipa--ipetqkgvifyenggelfykdipvpkp ScADH1   (SEQ ID NO:13)    30 kanellinvkysgvchtdlhawhgdwplpvklplvgghegagvvvgmgenvkgwkigdya
ScADH2   (SEQ ID NO:14)    30 kpnellinvkysgvchtdlhawhgdwplptklplvgghegagvvvgmgenvkgwkigdya
ScADH3   (SEQ ID NO:15)    57 kpneilinvkysgvchtdlhawhgdwplpvklplvgghegagvvvklgsnvkgwkvgdla
S141G2556 (SEQ ID NO:6)    32 kpteilvkvlysgvchtdlhawkgdwplatklplvgghegagvvvakgenvtsfeigdya
S141G9091 (SEQ ID NO:2)    52 kpteilinvkysgvchtdlhawkgdwplpaklplvgghegagivvakgsavtnfeigdya
S141G1202 (SEQ ID NO:4)    59 kpneilvnvkysgvchtdlhawkgdwplatklplvgghegagvvvakgdnvtnfeigdya ScADH1   (SEQ ID NO:13)    90 gikwlngscmaceycelgnesncphadlsgythdgsfqqyatadavqaahipqgtdlaqv
ScADH2   (SEQ ID NO:14)    90 gikwlngscmaceycelgnesncphadlsgythdgsfqeyatadavqaahipqgtdlaev
ScADH3   (SEQ ID NO:15)   117 gikwlngscmtcefcesghesncpdadlsgythdgsfqqfatadaiqaakiqqgtdlaev
S141G2556 (SEQ ID NO:6)    92 gikwlngscmgcefcceqgaepncpkadlsgythdgsfqqyatadaiqaahisketdlagv
S141G9091 (SEQ ID NO:2)   112 gikwlngscmscefcceqgdesncehadlsgythdgsfqqyatadaiqaakipkgtdlsev
S141G1202 (SEQ ID NO:4)   119 gikwlngscmgcefcqqgaepncpqadlsgythdgsfqqyatadavqaakipqgtdlaqv ScADH1   (SEQ ID NO:13)   150 apilcagitvykalksanlmaghwvaisgaagglgslavqyakamgyrvlgidggegkee
ScADH2   (SEQ ID NO:14)   150 apilcagitvykalksanlraghwaaisgaagglgslavqyakamgyrvlgidggpgkee
ScADH3   (SEQ ID NO:15)   177 apilcagvtvykalkeadlkagdwvaisgaagglgslavqyatamgyrvlgidageeekek
S141G2556 (SEQ ID NO:6)   152 apilcagvtvykalktadlragewvcisgaagglgslaiqyakamglrvvgidggdekke
S141G9091 (SEQ ID NO:2)   172 apilcagvtvykalktadlragqwvaisgaagglgslavqyakamglrvlgidggegkke
S141G1202 (SEQ ID NO:4)   179 apilcagitvykalktaelrpgqwvaisgaagglgslavqyakamglrvlgidggeekgk ScADH1   (SEQ ID NO:13)   210 lfrsiggevfidftk-----ekdivgavlkatdg-gahgvinvsvseaaieastryvran
ScADH2   (SEQ ID NO:14)   210 lftslggevfidftk-----ekdivsavvkatng-gahgiinvsvseaaieastrycran
ScADH3   (SEQ ID NO:15)   237 lfkklggevfidftk-----tknmvsdiqeatkg-gphgvinvsvseaaislsteyvrpc
S141G2556 (SEQ ID NO:6)   212 lckslgaeafidftk-----tkdivkavqeatng-gphgvinvsvseaaisqsceyvrpl
S141G9091 (SEQ ID NO:2)   232 lfeqcggdvfidftryprdapekmvadikaatnglgphgvinvsvspaaisqscdyvrat
S141G1202 (SEQ ID NO:4)   239 fakslgaevfidftk-----skdivkdiqeatng-gphgvinvsvspaaisqstqyvrtl ScADH1   (SEQ ID NO:13)   264 gttvlvgmpagakccsdvfnqvvksisivgsyvgnradtrealdffarglvkspikvvgl
ScADH2   (SEQ ID NO:14)   264 gtvvlvglpagakcssdvfnhvvksisivgsyvgnradtrealdffarglvkspikvvgl
ScADH3   (SEQ ID NO:15)   291 gtvvlvglpanayvksevfshvvksinikgsyvgnradtrealdffsrglikspikivgl
S141G2556 (SEQ ID NO:6)   266 gkvvlvglpagaqvktgvfeavvksieikgsyvgnrkdtaealdfytrglvkspfkivgl
S141G9091 (SEQ ID NO:2)   292 gkvvlvgmpsgavcksdvfthvvkslqikgsyvgnradtrealeffnegkvrspikvvpl
S141G1202 (SEQ ID NO:4)   293 gkvvlvglpahavcessvfdhvvksiqirgsyvgnredtseaidfftrglvkspikivgl ScADH1   (SEQ ID NO:13)   324 stlpeiyekmekgqivgryvvdtsk
ScADH2   (SEQ ID NO:14)   324 sslpeiyekmekgqiagryvvdtsk
ScADH3   (SEQ ID NO:15)   351 selpkvydlmekgkilgryvvdtsk
S141G2556 (SEQ ID NO:6)   326 selpkvfelmeqgkilgrmvldtsk
S141G9091 (SEQ ID NO:2)   352 stlpeiyelmeqgkilgryvvdtsk
S141G1202 (SEQ ID NO:4)   353 selpkiyelmeqgkilgryvvdtsk
```

COMPOSITIONS AND METHODS FOR INCREASED ETHANOL TITER FROM BIOMASS

CROSS REFERENCE TO RELATED APPLICATIONS

This application is a section 371 national-stage phase of International Application No. PCT/US2011/061955, filed 22 Nov. 2011, titled "COMPOUNDS AND METHODS FOR INCREASED ETHANOL TITER FROM BIOMASS" which claims priority to U.S. Application Ser. No. 61/416,169, filed 22 Nov. 2010, titled "COMPOUNDS AND METHODS FOR INCREASED ETHANOL TITER FROM BIOMASS," which is hereby incorporated by reference in their entirety.

GOVERNMENT INTEREST

This invention was made with governmental support under contract number DE-FC36-07 GO17055 awarded by the United States of America Department of Energy. The United States of America Government has certain rights in the invention.

BACKGROUND

A great deal of work has been performed in recent years to develop cost-effective methods for generating ethanol from biomass. The use of biomass to generate ethanol for fuel presents several advantages over the use of more traditional feedstock sources. The potential raw materials are abundant and diverse, the use of these feedstocks does not divert from the food supply, and they potentially exhibit a smaller carbon footprint.

Although biomass provides an attractive substrate for ethanol production, it also presents several challenges. First, biomass contains both cellulose, which can be broken down into the hexose sugar glucose, and hemicellulose, which can be broken down into both hexose sugars and pentose sugars such as xylose and arabinose. Many of the microorganisms traditionally used in ethanol fermentation are incapable of fermenting both hexose and pentose sugars to ethanol. Second, unlike more traditional sources of ethanol feedstock (e.g., corn, cane sugar), biomass includes structural components from plant sources. Because the source material is structural and more difficult to break down, biomass requires more processing to generate the sugar monomers that function as a fermentation substrate. Third, hydrolysate resulting from pre-treatment of biomass presents a harsh environment for fermenting microorganisms.

Several bacterial species are capable of fermenting pentose sugars to ethanol, but these species generally produce a mixture of products rather than a single product. Often one or more of these products are harmful to the bacteria. Further, bacteria can exhibit drastically reduced fermentation rates in the harsh environment of plant matter hydrolysate.

Yeast are generally considered to be more attractive candidates for industrial-scale ethanol fermentation than bacteria. However, very few yeast are capable of fermenting pentose sugars to ethanol. Various genetic modifications have been introduced into different yeast species in an attempt to overcome this problem. However, none of these previously developed modified strains have proven entirely satisfactory for large-scale ethanol production from biomass. Therefore, there is a need in the art for new genetically modified yeast strains capable of fermenting biomass to ethanol.

SUMMARY

Provided herein in certain embodiments are isolated *I. orientalis* ADH1, ADHa, and ADHb polynucleotides. In certain embodiments, these polynucleotides encode the amino acid sequence set forth in SEQ ID NO:2 (ADHa), SEQ ID NO:4 (ADHb), or SEQ ID NO:6 (ADH1). In other embodiments, the polynucleotides encode an amino acid sequence with at least about 90%, 95%, 96%, 97%, 98%, 99%, or 99.5% sequence identity to the amino acid sequences set forth in SEQ ID NOs:2, 4, or 6. In other embodiments, the polynucleotides encode an amino acid sequence with less than 90% sequence identity to the amino acid sequences set forth in SEQ ID NOs:2, 4, or 6, wherein the encoded polypeptide nonetheless has the ability to catalyze the conversion of acetaldehyde to ethanol or vice versa. In certain of these embodiments, the polynucleotides encode an amino acid sequence with at least about 70% sequence identity to the amino acid sequences set forth in SEQ ID NOs:2, 4, or 6. In certain embodiments, the polynucleotides provided herein comprise the DNA sequence of the coding region of SEQ ID NO:1 (ADHa), SEQ ID NO:3 (ADHb), or SEQ ID NO:5 (ADH1). In other embodiments, the polynucleotides comprise a DNA sequence with at least about 90%, 95%, 96%, 97%, 98%, 99%, or 99.5% sequence identity to the coding region of the DNA sequences set forth in SEQ ID NOs:1, 3, or 5. In still other embodiments, the polynucleotides provided herein comprise a DNA sequence with less than 90% sequence identity to the coding region of SEQ ID NOs:1, 3, or 5, but nonetheless encode a polypeptide with the ability to catalyze the conversion of acetaldehyde to ethanol or vice versa. Also provided herein are vectors comprising the polynucleotides provided herein, as well as host cells comprising these vectors.

Provided herein in certain embodiments are isolated *I. orientalis* ADH1, ADHa, and ADHb polypeptides. In certain embodiments, these polypeptides comprise the amino acid sequence set forth in SEQ ID NO:2 (ADHa), SEQ ID NO:4 (ADHb), or SEQ ID NO:6 (ADH1). In other embodiments, the polypeptides comprise an amino acid sequence with at least about 90%, 95%, 96%, 97%, 98%, 99%, or 99.5% sequence identity to the amino acid sequences set forth in SEQ ID NOs:2, 4, or 6. In still other embodiments, the polypeptides provided herein comprise an amino acid sequence with less than 90% sequence identity toe the amino acid sequences set forth in SEQ ID NOs:2, 4, or 6, but nonetheless have the ability to catalyze the conversion of acetaldehyde to ethanol and vice versa.

Provided herein in certain embodiments are methods of overexpressing *I. orientalis* ADH1 in a yeast cell by introducing one or more *I. orientalis* ADH1 polynucleotides. Similarly, provided herein in certain embodiments are genetically modified yeast cells that overexpress an *I. orientalis* ADH1 polypeptide. In certain embodiments, these yeast cells comprise a polynucleotide encoding the amino acid sequence set forth in SEQ ID NO:6. In other embodiments, the yeast cells comprise a polynucleotide encoding an amino acid sequence with at least about 90%, 95%, 96%, 97%, 98%, 99%, or 99.5% sequence identity to the amino acid sequence set forth in SEQ ID NO:6. In still other embodiments, the yeast cells comprise a polynucleotide that encodes an amino acid sequence with less than 90% sequence identity to the amino acid sequence set forth in SEQ ID NO:6, wherein the encoded polypeptide nonetheless has the ability to catalyze the conversion of ethanol to acetaldehyde. In certain embodiments, the yeast cells comprise a polynucleotide that comprises the DNA sequence of the coding region of SEQ ID NO:5. In other embodiments, the yeast cells comprise a polynucleotide that comprises a DNA sequence with at least about 90%, 95%, 96%, 97%, 98%, 99%, or 99.5% sequence identity to the coding region of the DNA sequences set forth in SEQ ID NO:5. In still other embodiments, the yeast cells comprise a polynucleotide that comprises a DNA sequence with less than 90% sequence identity to the coding region of SEQ ID NO:5, but which nonetheless encodes a polypeptide with the ability to catalyze the conversion of ethanol to acetaldehyde. In certain embodiments, ADH1 overexpression may be obtained through introduction of one or more exogenous ADH1 genes, increased expression of one or more endogenous ADH1 genes, or a combination thereof.

Provided herein in certain embodiments are methods of decreasing expression of *I. orientalis* ADHa and/or ADHb in a yeast cell by deleting or disrupting one or more endogenous *I. orientalis* ADHa and/or ADHb genes. Similarly, provided herein in certain embodiments are genetically modified yeast cells that comprise a deletion or disruption of one or more *I. orientalis* ADHa and/or ADHb genes. In certain embodiments, these yeast cells comprise a deletion or disruption of a polynucleotide encoding the amino acid sequence set forth in SEQ ID NO:2 (ADHa) or SEQ ID NO:4 (ADHb). In other embodiments, the yeast cells comprise a deletion or disruption of a polynucleotide encoding an amino acid sequence with at least about 90%, 95%, 96%, 97%, 98%, 99%, or 99.5% sequence identity to the amino acid sequence set forth in SEQ ID NOs:2 or 4. In still other embodiments, the yeast cells comprise a deletion or disruption of a polynucleotide that encodes an amino acid sequence with less than 90% sequence identity to the amino acid sequence set forth in SEQ ID NOs:2 or 4, wherein the encoded polypeptide nonetheless has the ability to catalyze the conversion of acetaldehyde to ethanol. In certain embodiments, the yeast cells comprise a deletion or disruption of a polynucleotide that comprises the DNA sequence of the coding region of SEQ ID NOs:1 or 3. In other embodiments, the yeast cells comprise a deletion or disruption of a polynucleotide that comprises a DNA sequence with at least about 90%, 95%, 96%, 97%, 98%, 99%, or 99.5% sequence identity to the coding region of the DNA sequences set forth in SEQ ID NOs:1 or 3. In still other embodiments, the yeast cells comprise a deletion or disruption of a polynucleotide that comprises a DNA sequence with less than 90% sequence identity to the coding region of SEQ ID NO:1 or 3, but which nonetheless encodes a polypeptide with the ability to catalyze the conversion of acetaldehyde to ethanol. In certain embodiments, deletion or disruption of one or more ADHa and/or ADHb genes may be coupled with introduction of one or more exogenous genes.

Provided herein in certain embodiments are genetically modified yeast cells that both overexpress an *I. orientalis* ADH1 polypeptide and comprise a deletion or disruption of one or more *I. orientalis* ADHa and/or ADHb genes.

In certain embodiments of the genetically modified yeast cells provided herein, the yeast cells belong to the *I. orientalis/P. fermentans* clade. In certain of these embodiments, the yeast cells are *I. orientalis*. In certain embodiments, the yeast cells may have undergone mutation and/or selection before, during, or after introduction of genetic modifications related to ADH1 overexpression and/or ADHa/ADHb deletion/disruption. In certain of these embodiments, the yeast cells may exhibit a degree of tolerance to ethanol, organic acids, other fermentation products or by-products, and/or various media components that is greater than that exhibited by wild-type yeast cells of the same species.

Provided herein in certain embodiments are fermentation processes wherein the genetically modified yeast cells provided herein are cultured in a fermentation medium that contains xylose. In certain of these embodiments, the fermentation medium contains at least about 10 g/L, 20 g/L, 30 g/L, 40 g/L, 50 g/L, 75 g/L, 100 g/L, or 125 g/L xylose. In certain embodiments, the xylose in the fermentation medium is derived from a plant biomass hydrolysate.

Provided herein in certain embodiments are methods of producing ethanol using the genetically modified yeast cells provided herein. In certain of these embodiments, the cells are cultured in a xylose-containing medium, and in certain of these embodiments the medium contains at least about 10 g/L, 20 g/L, 30 g/L, 40 g/L, 50 g/L, 75 g/L, 100 g/L, or 125 g/L xylose. In certain embodiments, the xylose in the medium is derived from a plant biomass hydrolysate.

BRIEF DESCRIPTION OF DRAWINGS

FIG. 15: Amino acid sequence alignment of *S. cerevisiae* ADH1, ADH2, and ADH3 with S141G2556, S141G9091, and S141G1202.

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

All references cited herein are incorporated by reference in their entirety.

ABBREVIATIONS

ADH, alcohol dehydrogenase; ALD, acetaldehyde dehydrogenase; CSH, corn stover hydrolysate; DM, defined media; DSP, D-xylulose 5-phosphate; F6P, fructose 6-phosphate; G3P, glyceraldehyde 3-phosphate; HMF, hydroxymethyl furfural; ORF, open reading frame; OUR, oxygen uptake rate; PPP, pentose phosphate pathway; RKI, ribose-5-phosphate ketol-isomerase; RPE, D-ribulose-5-phosphate 3-epimerase; TAL, transaldolase; TKL, transketolase; XDH, xylitol dehydrogenase; XK, xylulokinase; XR, xylose reductase; YP, yeast extract/peptone.

The ideal yeast species for industrial-scale ethanol production from biomass should exhibit resistance to low pH environments, the ability to ferment both hexose and pentose sugars to ethanol, and resistance to inhibitory compounds present in plant matter hydrolysate and arising from fermentation, including acetate, hydroxymethyl furfural (HMF), furfural, phenolics, aldehydes, ketones, and ethanol itself.

Figure 1:
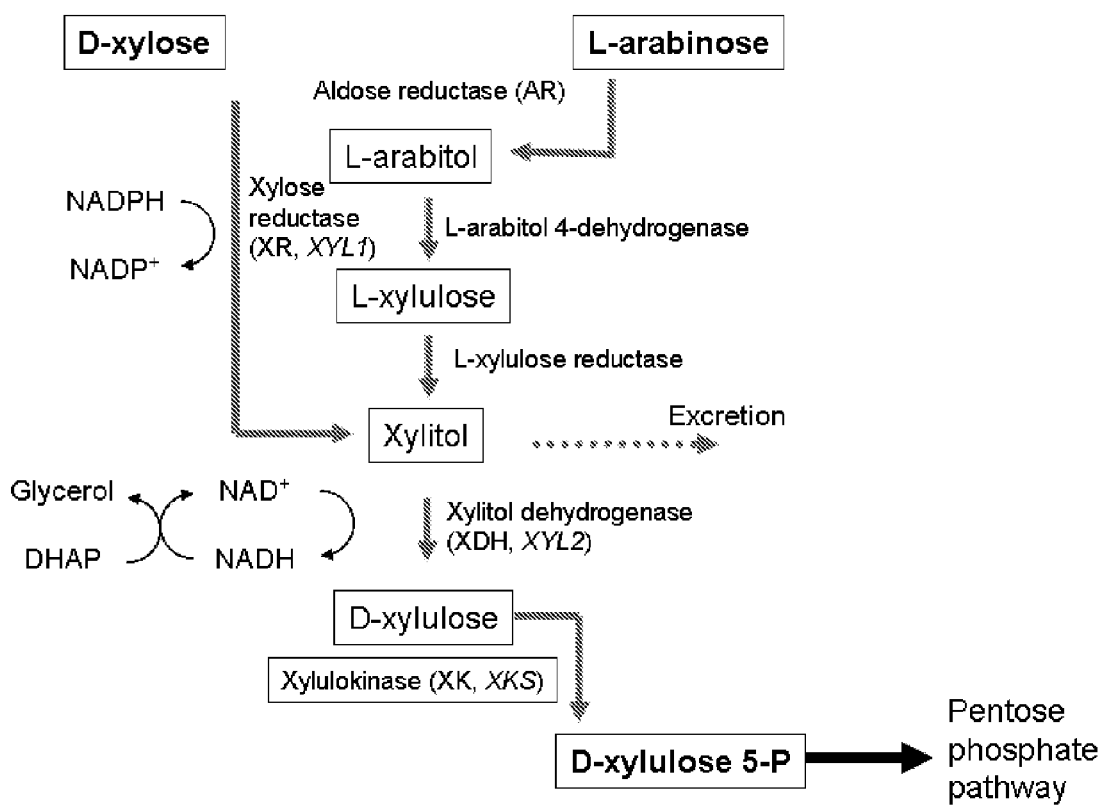
FIG. 1: Yeast xylose and arabinose fermentation pathways.

*S. cerevisiae* and most other yeast species are capable of fermenting hexose sugars to ethanol. However, the majority of yeast species are incapable of metabolizing pentose sugars. Those that are capable of metabolizing pentose sugars do so via a complex non-fermentative pathway. For example, yeast species that metabolize xylose, the predominant sugar in biomass, reduce D-xylose to xylitol using xylose reductase (XR). Xylitol is oxidized to D-xylulose by xylitol dehydrogenase (XDH), and D-xylulose is phosphorylated by xylulokinase (XK) to produce D-xylulose 5-phosphate (D5P). This pathway is illustrated in FIG. 1. The resultant D5P enters the pentose phosphate pathway (PPP), which generates fructose 6-phosphate (F6P) and glyceraldehyde 3-phosphate (G3P), both of which enter the glycolytic cycle.

Figure 2:
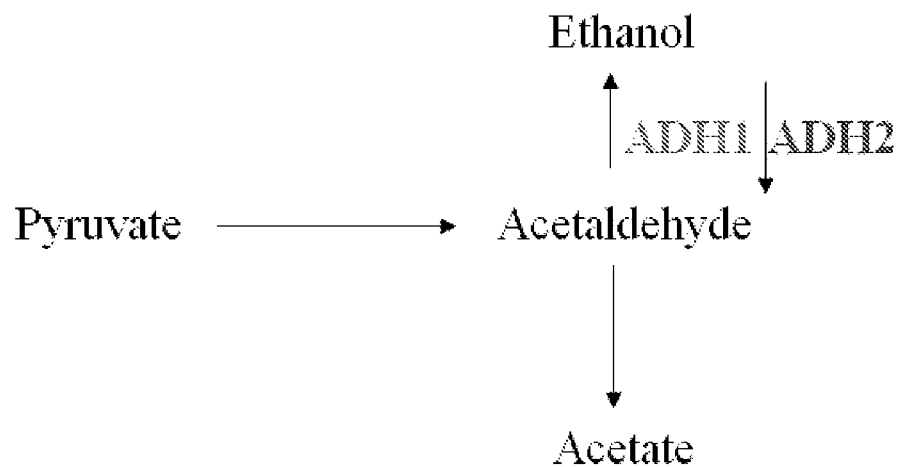
FIG. 2: Yeast pathway for conversion of pyruvate to ethanol.

Pyruvate arising from glycolysis is converted to acetaldehyde and $CO_2$ by pyruvate decarboxylase. The resultant acetaldehyde can either be reduced to ethanol by alcohol dehydrogenase (ADH) or converted to acetic acid by acetaldehyde dehydrogenase (ALD) (FIG. 2).

The xylose pathway in yeast is inefficient because it generates a redox imbalance. The conversion of xylose to xylitol uses NADPH as a cofactor, while the xylitol to xylulose step produces NADH. Under anaerobic conditions, more NADH is produced than can be recycled, and xylitol accumulates. Early attempts to genetically modify yeast to ferment xylose to ethanol more efficiently utilized exogenous XR and XDH genes (WO95/13362; WO97/42307). However, these modified organisms did not produce ethanol efficiently. Later attempts sought to circumvent the xylitol intermediate entirely by introducing an exogenous D-xylose isomerase (XI) gene and deleting XR and/or XDH (WO04/099381). XI converts xylose directly to xylulose, avoiding the generation of a redox imbalance. Pathways that utilize XI to metabolize xylose are common in bacteria, but rare in yeast. Genetically modified *K. marxianus* expressing exogenous *Piromyces* XI and overexpressing XK, and with deletions of endogenous XR and XDH genes, exhibited increased xylose utilization and ethanol production (WO04/099381).

In *Saccharomyces*, the main enzyme for ethanol production from acetaldehyde is ADH1. The reverse reaction of ethanol back to acetaldehyde is catalyzed primarily by ADH2, which has a higher affinity for ethanol than the other ADHs and is important in the use of ethanol as a carbon source. It has been reported previously that ADH1 is transcriptionally repressed in *Saccharomyces* in the absence of a fermentable carbon source, while ADH2 is repressed by glucose (Denis J Biol Chem 258:1165 (1983)). Genes for three additional ADHs (ADH3, ADH4, and ADH5) involved in ethanol metabolism in *Saccharomyces* have been identified, but their exact roles are unknown.

The function and regulation of ADHs across yeast species is not conserved. In *Kluyveromyces lactis*, four ADH genes have been identified. Two of these ADH genes are active in the cytoplasm, while the other two are active in the mitochondria. One of the mitochondrial ADHs has been shown to be induced by ethanol rather than repressed by glucose, approximating constitutive expression in fermenting strains. In *Pichia stipitis*, two cytoplasmic ADHs have been characterized. Expression of *P. stipitis* ADH1 appears to be induced approximately 10-fold by oxygen limitation. Although expression of *P. stipitis* ADH2 was low under both oxygen-limited and fully aerobic conditions, it was increased by disruption of ADH1, indicating feedback regulation of ADH2. Three cytoplasmic ADHs have been identified in *Candida maltosa*, two of which (ADH2a and ADH2b) are located tandem to one another on the genome. *C. maltosa* ADH1 is responsible for ethanol production from glucose, whereas ADH2a is glucose-repressed. However, both of these enzymes functioned in ethanol production from xylose. *C. maltosa* ADH2b is expressed at a lower level and its full function is yet to be determined.

As disclosed herein, three ADH genes from *I. orientalis* have been identified and characterized. The first two genes, referred to herein as ADHa and ADHb, encode ADH proteins that are expressed at a lower level under glucose conditions than the main *I. orientalis* fermentative enzyme, and exhibit ADH2-like properties under some but not all conditions. The DNA sequences of ADHa and ADHb are set forth in SEQ ID NOs:1 and 3, respectively. The coding region of ADHa (nucleotides 1052 to 2182 in SEQ ID NO:1) encodes the ADHa polypeptide set forth in SEQ ID NO:2, while the coding region of ADHb (nucleotides 1001 to 2134 in SEQ ID NO:3) encodes the ADHb polypeptide set forth in SEQ ID NO:4. Experimental results provided herein establish that knocking out ADHa and/or ADHb expression increases ethanol titer and xylose consumption in *I. orientalis* in xylose-containing media. The third ADH gene disclosed herein, ADH1, is functionally comparable to *S. cerevisiae* ADH1. The DNA sequence of the coding region of ADH1 is set forth in SEQ ID NO:5, and the amino acid sequence of the encoded polypeptide is set forth in SEQ ID NO:6. Experimental results provided herein establish that overexpression of ADH1 increases ethanol titer and xylose consumption in *I. orientalis* under many conditions. Therefore, provided herein are ADH1, ADHa, and ADHb polynucleotides and polypeptides, as well as vectors comprising ADH1, ADHa, and/or ADHb polynucleotides, host cells comprising these vectors, and methods of expressing ADH1, ADHa, and/or ADHb from these host cells.

Provided herein in certain embodiments are isolated ADHa, ADHb, and ADH1 polynucleotides. In certain embodiments, these isolated polynucleotides comprise a coding region encoding a polypeptide having the amino acid sequence set forth in SEQ ID NO:2, 4, or 6. In certain of these embodiments, the polynucleotides comprise the coding region of the nucleotide sequence set forth in SEQ ID NOs:1, 3, or 5. In other embodiments, the polynucleotides comprise a nucleotide sequence with at least 90% sequence identity to the coding region of the nucleotide sequence set forth in SEQ ID NOs:1, 3, or 5. In certain of these embodiments, the polynucleotides comprise a nucleotide sequence having at least 95%, at least 96%, at least 97%, at least 98%, at least 99%, or at least 99.5% sequence identity to the coding region of the nucleotide sequence set forth in SEQ ID NOs:1, 3, or 5.

Sequence identity percentages for nucleotide or amino acid sequences can be calculated by methods known in the art, such as for example using BLAST (National Center for Biological Information (NCBI) Basic Local Alignment Search Tool) version 2.2.1 software with default parameters. Sequences having an identity score of at least 90%, using the BLAST version 2.2.1 algorithm with default parameters are considered to have at least 90% sequence identity. The BLAST software is available from the NCBI, Bethesda, Md.

In certain embodiments, the isolated polynucleotides provided herein comprise a coding region encoding a polypeptide that comprises an amino acid sequence with at least 90% sequence identity to the amino acid sequence set forth in SEQ ID NOs:2, 4, or 6. In certain of these embodiments, the encoded polypeptide comprises an amino acid sequence with at least 95%, at least 96%, at least 97%, at least 98%, at least 99%, or at least 99.5% sequence identity to the amino acid sequence set forth in SEQ ID NOs:2, 4, or 6. In certain embodiments, the isolated polynucleotides comprise a nucleotide sequence with at least 90% sequence identity to the coding region of the nucleotide sequence set forth in SEQ ID NOs:1, 3, or 5. In certain of these embodiments, the isolated polynucleotides comprise a nucleotide sequence having at least 95%, at least 96%, at least 97%, at least 98%, at least 99%, or at least 99.5% sequence identity to the coding region of the nucleotide sequence set forth in SEQ ID NOs:1, 3, or 5.

In certain embodiments, isolated polynucleotides are provided that comprise a coding region encoding a polypeptide with 70% or greater sequence identity to the amino acid sequence set forth in SEQ ID NOs:2, 4, or 6, wherein the polypeptide is capable of catalyzing the conversion of ethanol to acetaldehyde or vice versa. As used herein, a polypeptide is considered to have the ability to catalyze conversion of acetaldehyde to ethanol if a test yeast cell overexpressing the polypeptide has at least 105% of the maximum increase in ethanol titer during consumption of 20 g/L or more of xylose in the absence of glucose compared to a control yeast cell, where the control yeast cell is genetically identical to the test yeast cell but for native expression of the polypeptide. Similarly, a polypeptide is considered to have the ability to catalyze the conversion of ethanol to acetaldehyde if a test yeast cell with a deletion of the gene encoding the polypeptide has at least 105% of the maximum increase in ethanol titer during consumption of 20 g/L or more of xylose in the absence of glucose compared to a control yeast cell, where the control yeast cell is genetically identical to the test yeast cell but without deletion of the gene encoding the polypeptide. In an exemplary protocol for establishing whether a test yeast cell has at least 105% of the maximum increase in ethanol titer during consumption of 20 g/L or more of xylose in the absence of glucose versus a control cell, overnight YPD cultures of the test and control cells are used to inoculate 50 mL of YP media containing 20 g/L dextrose and 80 g/L xylose at pH 4-6 in a 125 ml baffled flask to an initial $OD_{600}$ of 0.2 on a model DU600 spectrophotometer (Beckman Coulter) with a 1 cm path length. Cells are incubated at 30-37° C. and 100 rpm until dextrose is depleted and, subsequent to dextrose depletion, at least 20 g/L xylose is consumed.

In certain of these embodiments, the polynucleotides comprise a coding region encoding a polypeptide with at least 70%, at least 75%, at least 80%, at least 85%, or at least 90% sequence identity to the amino acid sequence set forth in SEQ ID NOs:2 or 4, wherein the polypeptide is capable of catalyzing the conversion of ethanol to acetaldehyde. In certain of these embodiments, the polynucleotides comprise a nucleotide sequence with at least 70%, at least 75%, at least 80%, at least 85%, or at least 90% sequence identity to the coding region of the nucleotide sequence set forth in SEQ ID NOs:1 or 3. In other embodiments, the polynucleotides comprise a coding region encoding a polypeptide with at least 70%, at least 75%, at least 80%, at least 85%, or at least 90% sequence identity to the amino acid sequence set forth in SEQ ID NO:6, wherein the polypeptide is capable of catalyzing the conversion of acetaldehyde to ethanol. In certain of these embodiments, the polynucleotide comprises a nucleotide sequence with at least 70%, at least 75%, at least 80%, at least 85%, or at least 90% sequence identity to the coding region of the nucleotide sequence set forth in SEQ ID NO:5.

Provided herein in certain embodiments are constructs comprising one or more of the isolated polynucleotides provided herein. The term "construct" as used herein refers to a DNA sequence that is used to transform a cell. The construct may be, for example, a circular plasmid or vector, a portion of a circular plasmid or vector (such as a restriction enzyme digestion product), a linearized plasmid or vector, or a PCR product prepared using a plasmid or vector as a template. In addition to one or more of the polynucleotides provided herein, a construct may comprise one or more regulatory elements (e.g., promoters, terminators) operatively linked to the polynucleotide sequence. The construct may further comprise one or more additional components, including for example one or more restriction sites and/or one or more selection marker genes, optionally linked to one or more regulatory elements. A "selection marker gene" is a gene that encodes a protein needed for the survival and/or growth of the transformed cell in a selective culture medium, and therefore can be used to apply selection pressure to the cell.

As used herein, the term "promoter" refers to an untranslated sequence located upstream (i.e., 5') to the translation start codon of a gene (generally within about 1 to 1000 base pairs (bp), preferably within about 1 to 500 bp) which controls the start of transcription of the gene. The term "terminator" as used herein refers to an untranslated sequence located downstream (i.e., 3') to the translation finish codon of a gene (generally within about 1 to 500 bp, preferably within about 1 to 300 bp, and especially within about 1 to 100 bp) which controls the end of transcription of the gene. A promoter or terminator is "operatively linked" to a gene if its position in the genome relative to that of the gene is such that the promoter or terminator, as the case may be, performs its transcriptional control function. Suitable promoters and terminators are described, for example, in WO99/14335, WO00/71738, WO02/42471, WO03/102201, WO03/102152 and WO03/049525 (all incorporated by reference herein in their entirety).

Further provided herein are host cells that have been transformed with one or more of the constructs provided herein, as well as methods of expressing ADHa, ADHb, and/or ADH1 from these host cells. In certain of these embodiments, the host cells are yeast or bacterial cells. In certain of those embodiments wherein the host cells are yeast cells, the yeast cells are Crabtree-negative yeast cells, and in certain of these embodiments the yeast cells belong to the genera *Candida* or *Issatchenkia*.

Provided herein in certain embodiments are isolated ADHa, ADHb, and ADH1 polypeptides. In certain embodiments, these polypeptides comprise the amino acid sequence set forth in SEQ ID NOs:2, 4, or 6. In other embodiments, the polypeptides comprise an amino acid sequence with at least 90% sequence identity to the amino acid sequence set forth in SEQ ID NOs:2, 4, or 6. In certain of these embodiments, the polypeptides comprise an amino acid sequence with at least 95%, at least 96%, at least 97%, at least 98%, at least 99%, or at least 99.5% sequence identity to the amino acid sequence set forth in SEQ ID NOs:2, 4, or 6. In still other embodiments, the polypeptides comprise an amino acid sequence with at least 70% sequence identity to the amino acid sequence set forth in SEQ ID NOs:2, 4, or 6 and also have the ability to catalyze the in vitro conversion of ethanol to acetaldehyde or vice versa. In certain of these embodiments, the polypeptides comprise an amino acid sequence with at least 70% sequence identity to the amino acid sequence set forth in SEQ ID NOs:2 or 4 and are capable of catalyzing the conversion of ethanol to acetaldehyde. In certain of these embodiments, the polypeptides comprise an amino acid sequence with at least 75%, at least 80%, at least 85%, or at least 90% sequence identity to the amino acid sequence set forth in SEQ ID NOs:2 or 4. In other embodiments, the polypeptides comprise an amino acid sequence with at least 70% sequence identity to the amino acid sequence set forth in SEQ ID NO:6 and are capable of catalyzing the conversion of acetaldehyde to ethanol. In certain of these embodiments, the polypeptides comprise an amino acid sequence with at least 75%, at least 80%, at least 85%, or at least 90% sequence identity to the amino acid sequence set forth in SEQ ID NO:6.

As disclosed herein, deletion or disruption of the ADHa and/or ADHb genes in *I. orientalis* resulted in a yeast strain with increased xylose utilization and ethanol titer versus parental strains in both synthetic medium and hydrolysate. As further disclosed herein, overexpression of the ADH1 gene in *I. orientalis* strains in which ADHa and/or ADHb have been deleted or disrupted produced a yeast strain that exhibits increased xylose utilization and ethanol titer versus a parental strain having only the deletion or disruption of ADHa and/or ADHb. As discussed above, the specific functional role and regulation of ADHs is not widely conserved among yeast species, and yeast ADHs exhibit significant variation with regard to their activity in the presence of glucose, ethanol, oxygen, and other potential regulators. In addition, the functionality of ADHs during fermentation of sugars that are not natively fermented by a host strain (e.g., pentose sugars) is largely unknown or has shown results divergent from those disclosed herein. For example, WO10/039,692 disclosed that ADH1 overexpression did not result in increased ethanol production in pentose sugar-containing media unless COX10 was also overexpressed. Similarly, it was previously shown that overexpression of ADH2 in *S. cerevisiae* did not result in the expected decrease in ethanol titer (Maestre 2008). Therefore, the effects of ADH1 overexpression and ADHa/ADHb deletion on xylose utilization and ethanol titer were unexpected. As such, provided herein are genetically modified yeast cells capable of fermenting xylose to ethanol and comprising one or more modifications to a gene that encodes a polypeptide capable of catalyzing the conversion of acetaldehyde to ethanol or the conversion of ethanol to acetaldehyde. These modifications may include deletion or disruption of one or more endogenous genes and/or overexpression of one or more endogenous or exogenous genes. In certain embodiments, the modifications include one or more of deletion or disruption of ADHa, deletion or disruption of ADHb, and overexpression of ADH1. Also provided herein are methods of making the genetically modified yeast cells provided herein and methods of using these genetically modified yeast cells to produce ethanol.

Provided herein in certain embodiments are genetically modified yeast cells that comprise a genome with a deletion or disruption of one or more endogenous genes encoding ADHa and/or ADHb and/or a deletion or disruption of one or more regulatory elements associated with such a gene. "Deletion or disruption" as used herein with regard to a gene means that the coding region of the gene is either eliminated entirely (deletion) or modified in such a way that the gene is either no longer capable of producing its encoded polypeptide or produces a polypeptide with markedly decreased activity (disruption). "Deletion or disruption" as used herein with regard to a regulatory element means that the regulatory element is eliminated entirely or modified in such a way that the gene to which it is operably linked no longer produces a functional polypeptide or produces a polypeptide with markedly decreased activity.

In certain embodiments, the genetically modified yeast cells provided herein comprise a deletion or disruption of one or more genes encoding a polypeptide comprising the amino acid sequence set forth in SEQ ID NOs:2 or 4 prior to deletion or disruption. In certain of these embodiments, the deleted or disrupted genes comprised the coding region of the nucleotide sequence set forth in SEQ ID NO:1 or 3 prior to deletion or disruption, while in other embodiments the deleted or disrupted genes comprised a nucleotide sequence with at least 90% sequence identity to the coding region of the nucleotide sequence set forth in SEQ ID NOs:1 or 3 prior to deletion or disruption. In certain of these embodiments, the deleted or disrupted genes comprised a nucleotide sequence having at least 95%, at least 96%, at least 97%, at least 98%, at least 99%, or at least 99.5% sequence identity to the coding region of the nucleotide sequence set forth in SEQ ID NOs:1 or 3 prior to disruption.

In certain embodiments, the deleted or disrupted genes encoded a polypeptide comprising an amino acid sequence with at least 90% sequence identity to the amino acid sequence set forth in SEQ ID NOs:2 or 4 prior to deletion or disruption. In certain of these embodiments, the encoded polypeptide comprised an amino acid sequence with at least 95%, at least 96%, at least 97%, at least 98%, at least 99%, or at least 99.5% sequence identity to the amino acid sequence set forth in SEQ ID NOs:2 or 4. In certain embodiments, the deleted or disrupted genes comprised a nucleotide sequence with at least 90% sequence identity to the coding region of the nucleotide sequence set forth in SEQ ID NOs:1 or 3 prior to deletion or disruption. In certain of these embodiments, the deleted or disrupted genes comprised a nucleotide sequence having at least 95%, at least 96%, at least 97%, at least 98%, at least 99%, or at least 99.5% sequence identity to the coding region of the nucleotide sequence set forth in SEQ ID NOs:1 or 3 prior to disruption.

In certain embodiments, the deleted or disrupted genes encoded a polypeptide with 70% or greater sequence identity to the amino acid sequence set forth in SEQ ID NOs:2 or 4 prior to deletion or disruption, wherein the encoded polypeptide had the ability to catalyze the conversion of ethanol to acetaldehyde in vitro or in vivo. In certain of these embodiments, the polypeptide comprised an amino acid sequence with at least 75%, at least 80%, at least 85%, or at least 90% sequence identity to the amino acid sequence set forth in SEQ ID NOs:2 or 4. In certain embodiments, the deleted or disrupted genes comprised a nucleotide sequence with at least 70% sequence identity to the coding region of the nucleotide sequence set forth in SEQ ID NOs:1 or 3 prior to deletion or disruption. In certain of these embodiments, the deleted or disrupted genes comprised a nucleotide sequence with at least 75%, at least 80%, at least 85%, or at least 90% sequence identity to the coding region of the nucleotide sequence set forth in SEQ ID NOs:1 or 3 prior to deletion or disruption.

Deletion or disruption of a target gene may be accomplished by any of a number of techniques known in the art. For example, a cell may be transformed with a deletion construct. A deletion construct may be assembled using two cloned target DNA sequences from the gene targeted for deletion or disruption or from its upstream (5') or downstream (3') flanking regions. The two DNA sequences from the target gene or its flanking regions are preferably non-contiguous, but may be contiguous if additional genetic material (such as a selection marker gene) is to be interposed between them in the deletion construct. In this context, "non-contiguous" means that the DNA sequences are not immediately adjacent to one another in the native genome, but are instead are separated by a region that is to be deleted in order to delete or disrupt the gene. "Contiguous" sequences as used herein are directly adjacent to one another in the native genome. One of the cloned sequences may include a region 5' to the promoter of the target gene, all or a portion of the promoter region, all or a portion of the target gene coding sequence, or some combination thereof. The other cloned sequence may include a region 3' to the terminator of the target gene, all or a portion of the terminator region, and/or all or a portion of the target gene coding sequence. The two cloned target sequences are incorporated into the deletion construct such that they are oriented in the same direction in relation to one another as they natively appear in the genome of the host cell.

A selection marker gene may be cloned into the deletion construct between the two target gene sequences to allow for selection of transformants. The selection marker gene may be incorporated into the deletion construct as part of an expression cassette that optionally includes one or more regulatory elements. Successful transformants will contain the selection marker gene, which imparts to the successfully transformed cell at least one characteristic that provides a basis for selection. Typical selection marker genes encode proteins that (a) confer resistance to antibiotics or other toxins (e.g., resistance to bleomycin or zeomycin (e.g., *Streptoalloteichus hindustanus* ble gene), aminoglycosides such as G418 or kanamycin (e.g., kanamycin resistance gene from transposon Tn903), or hygromycin (e.g., aminoglycoside antibiotic resistance gene from *E. coli*)), (b) complement auxotrophic deficiencies of the cell (e.g., deficiencies in leucine (e.g., *K. marxianus* LEU2 gene), uracil (e.g., *K. marxianus, S. cerevisiae,* or *I. orientalis* URA3 gene), or tryptophan (e.g., *K. marxianus, S. cerevisiae,* or *I. orientalis* TRP gene)), (c) enable the cell to synthesize critical nutrients not available from simple media, or (d) confer the ability for the cell to grow on a particular carbon source (e.g., MEL5 gene from *S. cerevisiae*, which encodes the alpha-galactosidase (melibiase) enzyme and confers the ability to grow on melibiose as the sole carbon source). Preferred selection markers include the zeocin resistance gene, G418 resistance gene, MEL5 gene, and hygromycin resistance gene. Another preferred selection marker is an L-lactate:ferricytochrome c oxidoreductase (CYB2) gene cassette, provided that the host cell either natively lacks such a gene or that its native CYB2 gene(s) are first deleted or disrupted.

In addition to selection marker genes, one or more other types of exogenous genes may be incorporated into a deletion construct. For example, one or more exogenous genes encoding enzymes involved in an ethanol fermentation pathway may be cloned into the deletion construct. Following transformation, the host cell will express this exogenous gene in lieu of the deleted or disrupted gene. As with selection marker genes, these additional exogenous genes may be incorporated into the deletion construct as part of an expression cassette that optionally contains one or more regulatory elements.

The deletion construct is used to transform the host cell. Methods for transforming a yeast cell with an exogenous DNA construct are described in, for example, WO99/14335, WO00/71738, WO02/42471, WO03/102201, WO03/102152, and WO03/049525. Transformation may be accomplished using any method known in the art, including for electroporation and/or chemical transformation (e.g., calcium chloride, lithium acetate-based, etc.) methods. Selection or screening may be performed to identify successful transformants. In successful transformants, a homologous recombination event at the locus of the target gene results in the disruption or the deletion of the target gene. All or a portion of the native target gene, its promoter, and/or its terminator may be deleted during this recombination event. If the deletion construct contains genetic material between the two cloned target gene sequences (e.g., selection marker cassette, expression cassette), that genetic material is inserted into the host cell's genome at the locus of the deleted material. Analysis by PCR or Southern analysis can be performed to confirm that the desired deletion or deletion/insertion has taken place.

Where a deletion construct comprises a selection marker gene, the construct may be designed such that the marker gene becomes spontaneously deleted as a result of a subsequent homologous recombination event. A convenient way of accomplishing this is to design the deletion construct such that the selection marker gene is flanked by direct repeat sequences. Direct repeat sequences are identical DNA sequences, native or non-native to the host cell, and oriented on the construct in the same direction with respect to one another. The direct repeat sequences are advantageously about 50 to 1500 bp in length, and do not have to encode for anything. Inclusion of the direct repeat sequences permits a homologous recombination event to occur, which results in deletion of the selection marker gene and one of the direct repeat sequences. Since homologous recombination occurs with relatively low frequency, it may be necessary to grow transformants for several rounds on nonselective media to allow for the spontaneous homologous recombination to occur in some of the cells. Cells in which the selection marker gene has become spontaneously deleted can be selected or screened on the basis of their loss of the selection characteristic imparted by the selection marker gene. In certain cases, expression of a recombinase enzyme may enhance recombination between the repeated sites.

Provided herein in certain embodiments are genetically modified yeast cells comprising a genetic modification that results in overexpression of ADH1, meaning that the cells express ADH1 at a higher level than a native cell under at least some conditions. The genetic modification that results in overexpression of ADH1 may be 1) introduction of one or more exogenous ADH1 genes into a host cell; 2) introduction of an exogenous regulatory element that increases expression of an endogenous or exogenous ADH1 gene in the host cell (e.g., a constitutive or inducible strong promoter sequence); or 3) a genetic modification that activates or increases the activity of a regulatory element associated with an exogenous or endogenous ADH1 gene; or any combination of the above. Accordingly, provided herein in certain embodiments are genetically modified yeast cells that comprise one or more exogenous or endogenous ADH1 genes. Further provided herein are genetically modified yeast cells that comprise one or more exogenous promoters that increase expression of an exogenous or endogenous ADH1 gene.

In certain embodiments, genetically modified yeast cells are provided that comprise one or more copies of an exogenous ADH1 gene. In certain of these embodiments, the cells further comprise one or more copies of an endogenous ADH1 gene. In these embodiments, introduction of one or more exogenous ADH1 genes into the cell increases ADH1 gene copy number. ADH1 may be expressed from both the endogenous and exogenous ADH1 genes equally, or the endogenous and exogenous ADH1 genes may be expressed at different levels. For example, the exogenous ADH1 genes may be expressed at a higher level than the endogenous ADH1 genes.

"Endogenous" as used herein with regard to genetic components such as genes, promoters, and terminator sequences means that the genetic component is present at a particular location in the genome of a native form of a particular yeast cell. "Exogenous" as used herein with regard to genetic components means that the genetic component is not present at a particular location in the genome of a native form of a particular yeast cell. "Native" as used herein with regard to a yeast cell refers to a wild-type yeast cell of a particular yeast species. "Native" as used herein with regard to a metabolic pathway refers to a metabolic pathway that exists and is active in a native yeast cell.

An exogenous genetic component may have either a native or non-native sequence. An exogenous genetic component with a native sequence comprises a sequence identical to (apart from individual-to-individual mutations which do not affect function) a genetic component that is present in the genome of a native cell (i.e., the exogenous genetic component is identical to an endogenous genetic component). However, the exogenous component is present at a different location in the host cell genome than the endogenous component. For example, an exogenous ADH1 gene that is identical to an endogenous ADH1 gene may be inserted into a yeast cell, resulting in a modified cell with a non-native (increased) number of ADH1 gene copies. An exogenous genetic component with a non-native sequence comprises a sequence that is not found in the genome of a native cell. For example, an exogenous gene from a particular species may be inserted into a yeast cell of another species. An exogenous gene is preferably integrated into the host cell genome in a functional manner, meaning that it is capable of producing an active protein in the host cell. However, in certain embodiments the exogenous gene may be introduced into the cell as part of a vector that is stably maintained in the host cytoplasm.

In certain embodiments, the genetically modified yeast cells provided herein that overexpress ADH1 comprise an exogenous or endogenous ADH1 gene that encodes a polypeptide comprising the amino acid sequence of SEQ ID NO:6. In certain of these embodiments, the ADH1 gene comprises the nucleotide sequence set forth in SEQ ID NO:5. In other embodiments, the ADH1 gene comprises a nucleotide sequence with at least 90% sequence identity to the nucleotide sequence set forth in SEQ ID NO:5. In certain of these embodiments, the polynucleotides comprise a nucleotide sequence having at least 95%, at least 96%, at least 97%, at least 98%, at least 99%, or at least 99.5% sequence identity to the nucleotide sequences set forth in any of SEQ ID NO:5.

In certain embodiments, the genetically modified yeast cells provided herein that overexpress ADH1 comprise an exogenous or endogenous ADH1 gene that encodes a polypeptide comprising an amino acid sequence with at least 90% sequence identity to the amino acid sequence set forth in SEQ ID NO:6. In certain of these embodiments, the polypeptide comprises an amino acid sequence with at least 95%, at least 96%, at least 97%, at least 98%, at least 99%, or at least 99.5% sequence identity to the amino acid sequence of SEQ ID NO:6. In certain embodiments, the ADH1 gene comprises a nucleotide sequence with at least 90% sequence identity to the nucleotide sequence set forth in SEQ ID NO:5. In certain of these embodiments, the ADH1 gene comprises a nucleotide sequence with at least 95%, at least 96%, at least 97%, at least 98%, at least 99%, or at least 99.5% sequence identity to the nucleotide sequence set forth in SEQ ID NO:5.

In certain embodiments, the genetically modified yeast cells provided herein that overexpress ADH1 comprise an exogenous or endogenous ADH1 gene that encodes a polypeptide comprising an amino acid sequence with at least 70% sequence identity to the amino acid sequence set forth in SEQ ID NO:6, wherein the encoded polypeptide has the ability to catalyze the conversion of acetaldehyde to ethanol in vitro or in vivo. In certain of these embodiments, the encoded polypeptide comprises an amino acid sequence with at least 75%, at least 80%, at least 85%, or at least 90% sequence identity to the amino acid sequence set forth in SEQ ID NO:6. In certain embodiments, the ADH1 gene comprises a nucleotide sequence with at least 70% sequence identity to the nucleotide sequence set forth in SEQ ID NO:5. In certain of these embodiments, the ADH1 gene comprises a nucleotide sequence with at least 75%, at least 80%, at least 85%, or at least 90% sequence identity to the nucleotide sequence set forth in SEQ ID NO:5.

In those yeast cells provided herein that comprise one or more copies of an exogenous ADH1 gene, the gene may be operatively linked to one or more regulatory elements such as a promoter or terminator. In certain embodiments, these regulatory elements may be native to the host cell, i.e., an exogenous gene may be inserted into a yeast cell such that it is under the transcriptional control of an endogenous promoter and/or terminator. In other embodiments, the regulatory elements may be exogenous. In these embodiments, the regulatory elements may have been introduced into the cell as part of the exogenous ADH1 gene expression construct. Promoters linked to one or more exogenous ADH1 genes may be strong promoters, such as constitutive or inducible promoters. In certain embodiments, exogenous promoters or terminators may be identical, or at least identical over their functional portions, to native promoter and terminator sequences. In other embodiments, exogenous promoters and terminators may comprise a nucleotide sequence that exhibits a relatively high degree of sequence identity to native promoter or terminator sequences. For example, an exogenous ADH1 gene may be operatively linked to an exogenous promoter or terminator with at least 50%, at least 60%, at least 70%, at least 80%, at least 90%, or at least 95% sequence identity to a native promoter or terminator. The native promoter or terminator to which the exogenous promoter or terminator exhibits this high degree of sequence identity may be natively linked to an endogenous ADH1 gene, to another gene involved in ethanol production, or to an unrelated gene. In those embodiments wherein multiple exogenous genes are inserted into a host cell, each exogenous gene may be under the control of a different promoter and/or terminator, or two or more exogenous genes may be under the control of the same promoter and/or terminator.

In those embodiments wherein the yeast cells provided herein comprise one or more copies of an exogenous ADH1 gene, the exogenous gene may be introduced via any method known in the art. The exogenous ADH1 gene may be integrated into the host cell genome in either a random or targeted manner. In those embodiments where the gene is integrated in a targeted manner, it may be integrated into the loci for a particular gene, such that integration of the exogenous gene is coupled to deletion or disruption of a native gene. For example, introduction of the exogenous ADH1 gene may be coupled to deletion of one or more genes involved in an ethanol production pathway, such as an ADHa or ADHb gene. Alternatively, the exogenous gene may be integrated into a portion of the genome that does not correspond to a gene.

Targeted integration may utilize a deletion construct as described above. In these methods, an ADH1 gene is incorporated into the construct between the two cloned target sequences. The ADH1 gene may be incorporated into the construct alone or as part of an expression cassette that comprises one or more regulatory elements such as promoters and/or terminators. Where the construct comprises a selection marker gene, the selection marker gene or cassette and the ADH1 gene or cassette may be contiguous or non-contiguous. In those embodiments wherein integration of the exogenous ADH1 gene is to be coupled with deletion or disruption of a target gene, the target sequences are derived from the target gene and/or its flanking regions. In those embodiments wherein integration of the exogenous ADH1 gene is not coupled to deletion or disruption of a target gene, target sequences are selected such that no gene spans the region between the target sequences. Following transformation of the host cell, the ADH1 gene is inserted into a target site by homologous recombination.

More than one copy of an exogenous ADH1 gene may be introduced into the yeast cell. For example, anywhere from one to ten copies of the ADH1 gene may be introduced. Where multiple copies of an ADH1 gene are introduced, the copies may be identical or they may vary with regard to the precise sequence of the ADH1 gene. The different copies of the exogenous ADH1 gene may be integrated into the yeast cell genome at a single location such that they are adjacent to one another, or they may be integrated at different locations. Each copy of the ADH1 gene may be linked to the same or different promoters, terminators, and/or selection markers.

In certain embodiments, genetically modified yeast cells are provided that comprise one or more exogenous promoters operatively linked to one or more endogenous ADH1 genes. In these embodiments, the exogenous promoter may replace or supplement a native promoter associated with the endogenous ADH1 gene. Incorporation of the exogenous promoters results in increased ADH1 expression versus native cells.

Although either deletion or disruption of ADHa and/or ADHb or overexpression of ADH1 alone is sufficient to increase xylose utilization and ethanol titer, the combination of both modifications resulted in a greater increase than either modification alone. Therefore, in certain embodiments genetically modified yeast cells are provided that comprise both a genome with a deletion or disruption of one or more endogenous genes encoding ADHa and/or ADHb and a genetic modification resulting in overexpression of ADH1. In certain embodiments, the genetic modification that results in overexpression of ADH1 is the presence of one or more copies of an exogenous ADH1 gene.

The genetically modified yeast cells provided herein may be selected from a variety of yeast species. In certain embodiments, the genetically modified yeast cells provided herein are non-*Saccharomyces* yeast cells. In certain of these embodiments, the yeast cells are Crabtree-negative yeast cells, and in certain of these embodiments the yeast cells belong to the *I. orientalis/P. fermentans* clade. The *I. orientalis/P. fermentans* clade is the most terminal clade that contains at least the species *I. orientalis*, *P. galeiformis*, P. sp. YB-4149 (NRRL designation), *C. ethanolica*, *P. deserticola*, *P. membranifaciens*, and *P. fermentans*. Members of the *I. orientalis/P. fermentans* clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences," Antonie van Leeuwenhoek 73:331-371, 1998, incorporated herein by reference (see especially p. 349). Analysis of the variable D1/D2 domain of the 26S ribosomal DNA from hundreds of ascomycetes has revealed that the *I. orientalis/P. fermentans* clade contains very closely related species. Members of the *I. orientalis/P. fermentans* clade exhibit greater similarity in the variable D1/D2 domain of the 26S ribosomal DNA to other members of the clade than to yeast species outside of the clade. Therefore, other members of the *I. orientalis/P. fermentans* clade can be identified by comparison of the D1/D2 domains of their respective ribosomal DNA and comparing to that of other members of the clade and closely related species outside of the clade, using Kurtzman and Robnett's methods. In certain embodiments, the genetically modified yeast cells provided herein belong to the genus *Issatchenkia*, and in certain of these embodiments the yeast cells are *I. orientalis*. When first characterized, the species *I. orientalis* was assigned the name *Pichia kudriavzevii*. The anamorph (asexual form) of *I. orientalis* is known as *Candida krusei*. Numerous additional synonyms for the species *I. orientalis* have been listed elsewhere (Kurtzman and Fell, The Yeasts, a Taxonomic Study. Section 35. *Issatchenkia Kudryavtsev*, pp 222-223 (1998)). *I. orientalis* and other members of the *I. orientalis/P. fermentans* clade exhibit certain characteristics that make them ideal for ethanol fermentation from biomass, including tolerance to low pH, ethanol, high temperature (40° C. or greater), and various inhibitors present in hydrolysate.

As set forth in the examples below, ADH1, ADHa, and ADHb expression analysis was carried out using an *I. orientalis* strain (strain 1822) that had previously been selected for resistance to 2-hydroxypropionic acid. Accordingly, in certain embodiments the genetically modified yeast cells provided herein may have undergone mutation and/or selection for resistance to ethanol, organic acids, other fermentation products or by-products, or media components such as acetate. Selection may be carried out before, during, or after introduction of genetic modifications relating to ADH1, ADHa, and/or ADHb using methods known in the art. For example, selection may be carried out using a chemostat. A chemostat is a device that allows for a continuous culture of microorganisms (e.g., yeast) wherein the specific growth rate and cell number can be controlled independently. A continuous culture is essentially a flow system of constant volume to which medium is added continuously and from which continuous removal of any overflow can occur. Once such a system is in equilibrium, cell number and nutrient status remain constant, and the system is in a steady state. A chemostat allows control of both the population density and the specific growth rate of a culture through dilution rate and alteration of the concentration of a limiting nutrient, such as a carbon or nitrogen source. By altering the conditions as a culture is grown (e.g., decreasing the concentration of a secondary carbon source necessary to the growth of the inoculum strain, among others), microorganisms in the population that are capable of growing faster at the altered conditions will be selected and will outgrow microorganisms that do not function as well under the new conditions. Typically such selection requires the progressive increase or decrease of at least one culture component over the course of growth of the chemostat culture. The operation of chemostats and their use in the directed evolution of microorganisms is well known in the art (see, e.g., Novick Proc Natl Acad Sci USA 36:708-719 (1950), Harder J Appl Bacteriol 43:1-24 (1977).

In certain embodiments, the yeast cells provided herein comprise one or more genetic modifications in addition to ADH1 overexpression and/or ADHa/ADHb deletion or disruption. These additional genetic modifications may include one or more of the following: overexpression of XI; overexpression of XK; deletion or disruption of one or more genes encoding a polypeptide with XR activity; deletion or disruption of one or more genes encoding polypeptides with XDH activity; overexpression of one or more genes in the nonoxidative pentose phosphate pathway (transaldolase (TAL), transketolase (TKL), D-ribulose-5-phosphate 3-epimerase (RPE), ribulose 5-phosphate ketol-isomerase (RKI)); expression of one or more genes in an arabinose consumption pathway; expression of a pentose transporter; and deletion or disruption of one or more genes involved in the conversion of acetaldehyde to acetic acid, such as ALD.

Provided herein in certain embodiments are methods of producing a genetically modified yeast cell capable of fermenting xylose to ethanol by deleting or disrupting one or more endogenous genes encoding ADHa and/or ADHb. In certain embodiments, the deleted or disrupted genes encoded a polypeptide comprising the amino acid sequence set forth in SEQ ID NOs:2 or 4 prior to deletion or disruption. In certain of these embodiments, the deleted or disrupted genes comprised the coding region of the nucleotide sequence set forth in SEQ ID NO:1 or 3 prior to deletion or disruption, while in other embodiments the deleted or disrupted genes comprised a nucleotide sequence with at least 90%, at least 95%, at least 96%, at least 97%, at least 98%, at least 99%, or at least 99.5% sequence identity to the coding region of the nucleotide sequence set forth in SEQ ID NOs:1 or 3 prior to deletion or disruption. In certain embodiments, the deleted or disrupted genes encoded a polypeptide comprising an amino acid sequence with at least 90%, at least 95%, at least 96%, at least 97%, at least 98%, at least 99%, or at least 99.5% sequence identity to the amino acid sequence set forth in SEQ ID NOs:2 or 4 prior to deletion or disruption, and in certain of these embodiments the deleted or disrupted gene comprised a nucleotide sequence with at least 90%, at least 95%, at least 96%, at least 97%, at least 98%, at least 99%, or at least 99.5% sequence identity to the coding region of the nucleotide sequence set forth in SEQ ID NOs:1 or 3. In certain embodiments, the deleted or disrupted genes encoded a polypeptide comprising an amino acid sequence with at least 70% sequence identity to the amino acid sequence set forth in SEQ ID NOs:2 or 4 prior to deletion or disruption, wherein the polypeptide was capable of catalyzing the conversion of ethanol to acetaldehyde. In certain of these embodiments, the encoded polypeptide comprised an amino acid sequence with at least 75%, at least 80%, at least 85%, or at least 90% sequence identity to the amino acid sequence in SEQ ID NOs:2 or 4. In certain of these embodiments, the deleted or disrupted genes comprised a nucleotide sequence with at least 70%, at least 75%, at least 80%, at least 85%, or at least 90% sequence identity to the coding region of the nucleotide sequence set forth in SEQ ID NOs:1 or 3 prior to deletion or disruption. In certain embodiments, one or more additional genetic modifications are introduced into the yeast cells in addition to deletion or disruption of one or more ADHa and/or ADHb genes. In certain of these embodiments, the cells are modified to overexpress ADH1. In certain of these embodiments, overexpression of ADH1 is accomplished by introducing one or more copies of an exogenous ADH1 gene. In other embodiments, overexpression is accomplished by increasing expression from one or more endogenous copies of the ADH1 gene that are already present in the cell.

Provided herein in certain embodiments are methods of producing a genetically modified yeast cell capable of fermenting xylose to ethanol by introducing a genetic modification that results in overexpression of ADH1. ADH1 may be overexpressed from one or more exogenous genes, one or more endogenous genes, or a combination thereof. Therefore, in certain embodiments these methods comprise introducing one or more exogenous ADH1 genes into a host yeast cell such that the cell comprises one or more copies of an exogenous ADH1 gene. In certain embodiments, the ADH1 gene being overexpressed encodes a polypeptide comprising the amino acid sequence of SEQ ID NO:6. In certain of these embodiments, the ADH1 gene being overexpressed comprises the nucleotide sequence set forth in SEQ ID NO:5. In other embodiments, the ADH1 gene comprises a nucleotide sequence with at least 90%, at least 95%, at least 96%, at least 97%, at least 98%, at least 99%, or at least 99.5% sequence identity to the nucleotide sequence set forth in SEQ ID NO:5. In certain embodiments, the ADH1 gene being overexpressed encodes a polypeptide comprising an amino acid sequence with at least 90%, at least 95%, at least 96%, at least 97%, at least 98%, at least 99%, or at least 99.5% sequence identity to the amino acid sequence set forth in SEQ ID NO:6. In certain of these embodiments, the ADH1 gene being overexpressed comprises a nucleotide sequence with at least 90% sequence identity to the nucleotide sequence set forth in SEQ ID NO:5. In certain embodiments, the ADH1 gene being overexpressed encodes a polypeptide comprising an amino acid sequence with at least 70% sequence identity to the amino acid sequence set forth in SEQ ID NO:6, wherein the polypeptide is capable of catalyzing the conversion of acetaldehyde to ethanol. In certain of these embodiments, the polypeptide comprises an amino acid sequence with at least 75%, at least 80%, at least 85%, or at least 95% sequence identity to the amino acid sequence of SEQ ID NO:6. In certain of these embodiments, the ADH1 gene being overexpressed comprises a nucleotide sequence with at least 70%, at least 75%, at least 80%, at least 85%, or at least 90% sequence identity to the nucleotide sequence set forth in SEQ ID NO:5. In certain embodiments, one or more additional genetic modifications are introduced into the yeast cells in addition to modifications resulting in the overexpression of ADH1. In certain of these embodiments, the cells are modified by deleting or disrupting one or more ADHa or ADHb genes.

In certain embodiments, fermentation processes are provided wherein a genetically modified yeast cell as provided herein is cultured under fermentation conditions. In certain embodiments, the yeast cells comprise a genome with a deletion or disruption of one or more genes encoding ADHa and/or ADHb. In other embodiments, the yeast cells comprise a genetic modification that results in overexpression of ADH1, and in certain of these embodiments the yeast cells comprise one or more copies of an exogenous ADH1 gene. In certain embodiments, the yeast cells comprise a combination of genetic modifications resulting in overexpression of ADH1 and deletion or disruption of one or more genes encoding ADHa and/or ADHb. In certain of these embodiments, the fermentation process results in the production of ethanol.

In certain embodiments, methods are provided for producing ethanol by culturing a genetically modified yeast cell as provided herein with one or more pentose and/or hexose sugars. In certain embodiments, the yeast cells comprise a genome with a deletion or disruption of one or more genes encoding ADHa and/or ADHb. In other embodiments, the yeast cells comprise a genetic modification that results in overexpression of ADH1. In certain of these embodiments, the yeast cells comprise one or more copies of an exogenous ADH1 gene. In certain embodiments, the yeast cells comprise a combination of genetic modifications resulting in overexpression of ADH1 and deletion or disruption of one or more genes encoding ADHa and/or ADHb.

In certain embodiments of the processes and methods provided herein, the media used for culturing the genetically modified yeast cells provided herein comprises one or more non-glucose sugars that are fermentable by the cells. In certain of these embodiments, the non-glucose sugars may be xylose, xylan, another oligomer of xylose, and/or arabinose. These non-glucose sugars may be hydrolysates of a hemicellulose-containing biomass such as a plant biomass hydrolysate. The media may further comprise glucose and/or oligomers or polymers of glucose. Where multimeric sugars are present, it may be necessary to add enzymes to the fermentation broth to digest these sugars to the corresponding monomeric sugar.

In certain embodiments of the process and methods provided herein, the media used for culturing the genetically modified yeast cells provided herein is a xylose-containing medium, and in certain of these embodiments the xylose is derived from a plant biomass hydrolysate. In certain embodiments, xylose may be present in the medium at a concentration of about 0 to about 150 g/L at the outset of fermentation (i.e., at or before the point at which the cells are added to the medium) and/or at various timepoints during the fermentation process. In certain of these embodiments, xylose may be present in the medium at a concentration of at least about 10 g/L, 20 g/L, 30 g/L, 40 g/L, 50 g/L, 75 g/L, 100 g/L, or 125 g/L. In certain embodiments, the media may comprise one or more sugars in addition to xylose, including one or more pentose and/or hexose sugars. In certain of these embodiments, xylose may make up about 10 to about 95% of the total sugar content of the medium at the outset of fermentation and/or at various timepoints during the fermentation process. In certain of these embodiments, xylose may make up at least about 10%, 20%, 30%, 40%, 50%, 60%, 70%, 80%, or 90% of the total sugar content of the medium. In certain embodiments, the genetically modified yeast cells may ferment one or more of the additional sugars present in the media to ethanol.

In certain embodiments of the process and methods provided herein, the media is a synthetic media such as a yeast extract/peptone media, and in certain of these embodiments the media may contain acetate. In other embodiments, the media is a defined synthetic media, and in certain of these embodiments the media may contain acetate. In certain embodiments, the media comprises some percentage of biomass hydrolysate, such as corn stover hydrolysate. In these embodiments, hydrolysate may be present in the medium at anywhere from about 10% to 100% of the total medium volume. In certain of these embodiments, the hydrolysate may have been pre-treated. For example, the hydrolysate may have been pre-treated with one or more acids or enzymes in order to partially break down the feedstock. In certain embodiments, the hydrolysate is undetoxified hydrolysate. In those embodiments wherein the medium comprises hydrolysate at less than 100%, the remainder of the medium may comprise one or more diluting agents including synthetic medium or water.

In certain embodiments, culturing of the cells provided herein to produce ethanol may be divided up into phases. For example, the cell culture process may be divided into a cultivation phase, a production phase, and a recovery phase. One of ordinary skill in the art will recognize that these conditions may be varied based on factors such as the species of yeast being used, the specific fermentation pathway utilized by the yeast, the desired yield, or other factors.

In certain embodiments of the processes and methods provided herein, cells are cultured at a temperature of about 20° C. to about 60° C. In certain of these embodiments, fermentation takes place at a temperature ranging from about 30° C. to about 50° C., and in certain of these embodiments fermentation takes place at a temperature from about 35° C. to about 45° C. Temperature may be varied throughout the fermentation process.

The fermentation may be conducted aerobically, microaerobically, substantially anaerobically, or anaerobically. If desired, oxygen uptake rate can be varied throughout fermentation as a process control (see, e.g., WO03/102200). In certain preferred embodiments, fermentation may take place under microaerobic conditions, which are characterized by an oxygen uptake rate from about 2 to about 25 mmol/L/h.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Identification of *I. orientalis* ADH1, ADHa, and ADHb Genes

The ADH2 amino acid sequence from *S. cerevisiae* was used to perform a Blast search of the wild-type *I. orientalis* genome. Three putative homologs were identified: open reading frames (ORFs) S141G9091, S141G1202, and S141G2556. S141G9091 had the DNA sequence set forth SEQ ID NO:1. The coding region of S141G9091 (nucleotides 1052 to 2182 of SEQ ID NO:1) encodes the polypeptide sequence set forth in SEQ ID NO:2. S141G1202 had the DNA sequence set forth in SEQ ID NO:3. The coding region of S141G1202 (nucleotides 1001 to 2134 of SEQ ID NO:3) encodes the polypeptide sequence set forth in SEQ ID NO:4. The coding region of S141G2556 had the DNA sequence set forth SEQ ID NO:5, and encodes the polypeptide sequence set forth in SEQ ID NO:6.

Alignments of the *I. orientalis* homologs with characterized ADH homologs from *Saccharomyces* and other yeast species showed the homologs to all be approximately equal in similarity to ADH1, ADH2 and ADH3 homologs. FIG. 15 shows an amino acid sequence alignment of S141G9091 (SEQ ID NO:2), S141G1202 SEQ ID NO:4), and S141G2556 (SEQ ID NO:6) with *S. cerevisiae* ADH1 (SEQ ID NO:13), ADH2 (SEQ ID NO:14), and ADH3 (SEQ ID NO:15). Table 1 summarizes the percent identity between the amino acid sequences of S141G9091, S141G1202, and S141G2556 and *S. cerevisiae* ADH1, ADH2, and ADH3. S141G9091 and S141G1202 both possess an N-terminal extension that may be indicative of an organellar targeting sequence.

TABLE 1

Percent identity between amino acid sequences

|  | S141G2556 | S141G9091 | S141G1202 |
|---|---|---|---|
| ScADH1 | 73% | 70% | 71% |
| ScADH2 | 74% | 69% | 71% |
| ScADH3 | 70% | 71% | 75% |

Because of the similarities in homology between the pairwise comparisons, RNA expression was analyzed in *I. orientalis* strain 1822 to identify which homolog was the main fermentative ADH and which might be involved in ethanol consumption. Strain 1822 is a 2-hydroxypropionic acid-resistant strain that was obtained by evolving *I. orientalis* strain ATCC PTA-6658 in a glucose-limited chemostat. During this process, the system was fed with 15 g/L dextrose in a DM medium, and operated at a dilution rate of 0.06 $h^{-1}$ at pH 3.0 with added 2-hydroxypropionic acid in the feed medium. Conditions were maintained with a low oxygen transfer rate of approximately 2 mmol $L^{-1}$ $h^{-1}$, and dissolved oxygen concentration remained constant at 0% of air saturation. The concentration of 2-hydroxypropionic acid in the feed medium was increased in 5 g/L increments approximately every two weeks from an initial concentration of 30 g/L to a final concentration of 60 g/L. Single colony isolates from the final time point were characterized in two shake flask assays. In the first assay, the strains were characterized for their ability to ferment glucose to ethanol in the presence of 25 g/L free 2-hydroxypropionic acid. In the second assay, the growth rates of the isolates were measured in the presence of 25, 32 and 45 g/L of total 2-hydroxypropionic acid with no pH adjustment. Strain 1822 represented a single isolate that was selected based on the measured fermentation and growth rates.

To obtain biomass for expression analysis, an overnight culture of *I. orientalis* strain 1822 grown on YPD (YP (10 g/L yeast extract and 20 g/L peptone)-based media containing 100 g/L dextrose) media was spun down, washed, and used to inoculate 50 mL flasks (50 mL YP media in 250 mL flasks) containing either 2% ethanol or 2% glucose. Cultures were grown at 37° C. and 250 rpm to an $OD_{600}$ of 2.0, and 10 mL samples were spun down and frozen in liquid nitrogen. RNA was isolated and used to derive cDNA using reverse transcriptase (Promega). Quantitative PCR was performed using primers specific to each homolog (S141G9091: SEQ ID NO:9 (forward), SEQ ID NO:10 (reverse); S141G1202: SEQ ID NO:11 (forward), SEQ ID NO:12 (reverse); S141G2556: SEQ ID NO:7 (forward), SEQ ID NO:8 (reverse). Results are summarized in Table 2. One of the three homologs (S141G9091) showed expression only with ethanol as a substrate. The other two homologs (S141G1202 and S141G2556) showed expression with both ethanol and glucose substrates, although the expression level of S141G1202 was much lower than that of S141G2556.

TABLE 2

C(t) values in glucose and ethanol cultures

|  | Glucose | Ethanol |
|---|---|---|
| S141G1202 | 33.1, 33.2 | 34.2, 34.0 |
| S141G9091 | N/A | 28.3, 28.5 |
| S141G2556 | 27.3, 27.4 | 28.4, 28.6 |
| actin | 36.5 | 35.8/37.4 |

Microarray (Nimblegen) expression analysis was run on xylose-fermenting strain 3556 (derived from strain 1822) grown in fermentors in YP media with glucose, xylose, or a mixture of glucose and xylose as the carbon source. The dissolved oxygen concentration in these fermentations was measured using a polarographic dissolved oxygen electrode. The dissolved oxygen concentration is expressed as a percentage of the saturated concentration of oxygen in the fermentation medium under air at an ambient pressure of 1 atmosphere. Samples for RNA extraction were taken two hours after the dissolved oxygen reached zero percent for the cultures grown on glucose, five hours after dissolved oxygen reached zero percent for cultures grown on a glucose-xylose mix, and ten hours after dissolved oxygen reached zero percent for cultures grown on xylose. The normalized expression levels for the three loci are shown in Table 3.

TABLE 3

Normalized expression levels in
glucose, xylose, and glucose/xylose cultures

|  | Glucose | Xylose | Glucose + Xylose |
|---|---|---|---|
| S141G1202 | 1551 | 54362 | 808 |
| S141G9091 | 17092 | 15446 | 25412 |
| S141G2556 | 39781 | 32743 | 47484 |

Based on the expression levels and patterns, it was concluded that S141G2556 represents the main fermentative ADH enzyme. S141G2556 was therefore designated as *I. orientalis* ADH1. The other two homologs exhibited low expression in the presence of glucose under at least some conditions, behavior more consistent with a role in ethanol consumption. However, since this behavior was not consistent across expression studies, these homologs were designated as *I. orientalis* ADHa (S141G9091) and ADHb (S141G1202).

Example 2

Characterization of ADHa Using Gene Knockouts

In order to confirm the role of ADHa in ethanol metabolism, an *I. orientalis* strain was developed with both copies of ADHa knocked out. The regions upstream and downstream of ADHa (~0.5-1 Kb) were amplified from genomic DNA and cloned into a TOPO vector separated by a NotI site. The upstream product was digested with KpnI and NotI, and the downstream product was digested with NotI and ApaI. The TOPO vector was digested with ApaI and KpnI and gel purified, and the two digested PCR products were ligated into the TOPO vector. The ligation reaction was transformed into *E. coli*, and plasmid DNA from individual colonies was screened for the correct DNA sequence. A NotI fragment carrying the *I. orientalis* URA3 selection cassette was inserted into the TOPO vector to create vectors pHJJ27 (orientation 1) and pHJJ28 (orientation 2). The URA3 selection cassette consists of the URA3 gene and its regulatory elements flanked by direct repeat sequences to allow marker recycling and reuse.

pHJJ27 was digested with ApaI and KpnI to release the integration fragment, and the resultant linearized DNA was transformed into *I. orientalis* strain 3098 (ura-derivative of strain 3082), which contained four copies of an exogenous gene encoding *B. thetaiotaomicron* XI, two copies of a native exogenous gene encoding XK, and two copies of a native exogenous gene encoding TAL, along with deletions at the XR and XDH loci. Exogenous XI genes were incorporated because *I. orientalis* lacks a native pathway for fermenting xylose. Insertion into the ADHa locus was confirmed in the resultant strain (strain 3274) by PCR across both integration junctions. Strain 3274 was grown overnight in YPD and plated on FOA media. The ura-phenotype was confirmed by plating on ScD-ura media, and retention of the integration was confirmed by PCR. The resultant ura-strain was labeled 3284.

pHJJ28 was digested with ApaI and KpnI to release the integration fragment, and the resultant linearized DNA was transformed into *I. orientalis* strain 3284. Strain 3085 was identified as containing two copies of the knockout/no wild-type loci.

Growth and fermentation of strain 3085 versus parental strain 3082 was evaluated in a shake flask. The media was YP (10 g/L yeast extract and 20 g/L peptone) based with 0.5 g/L $MgSO_4$, trace elements, and vitamins, and brought to pH 5.1 with $H_2SO_4$. Fermentations were run with 50 mL of media in 125 mL flasks at 37° C. with shaking at 100 RPM. Deletion of ADHa was shown to have little impact on dextrose or xylose utilization in YP media containing 20 g/L dextrose, 40 g/L xylose, and 9 g/L acetate (YP20D40X9Ac), while enhancing ethanol rate by 16% and specific ethanol rate by 10%. Greater effects were observed for the knockout strain using YP media containing 60 g/L xylose (YP60X). Under these conditions, strain 3085 had a xylose utilization rate of 0.46 g/L/hr compared to 0.14 for parent strain 3082, and an ethanol production rate of 0.46 g/L/hr compared to 0.024 for the parent strain. These results indicate that ADHa is involved in ethanol consumption and is more highly expressed during growth on xylose than with glucose present.

Example 3

Characterization of ADHb Using Gene Knockouts

Figure 3:
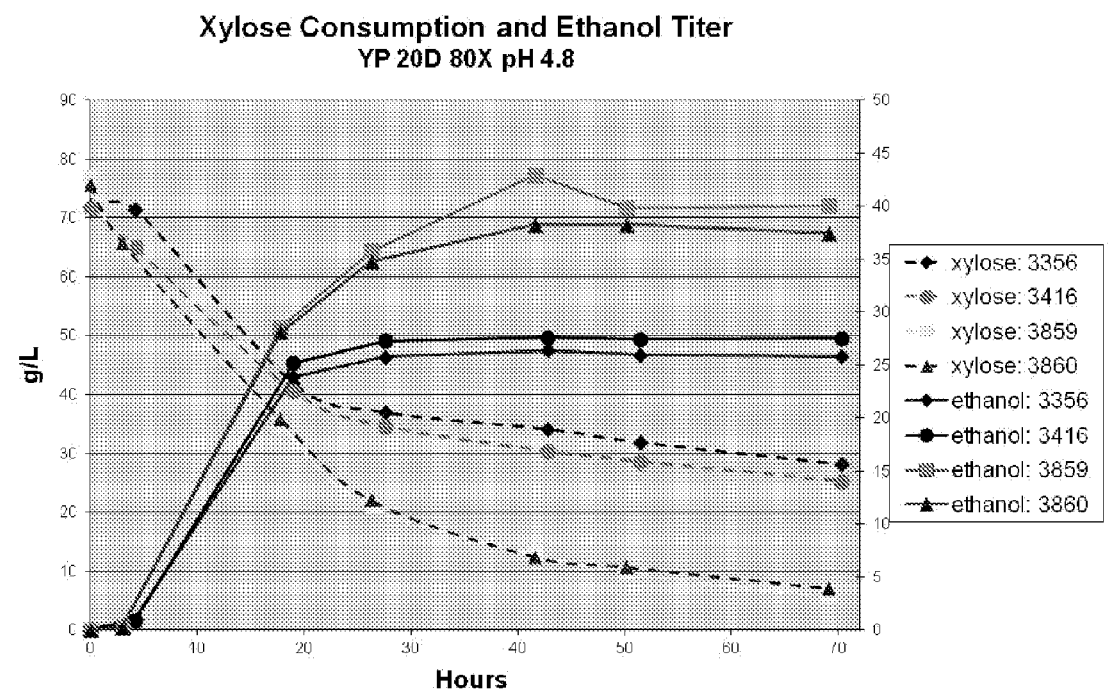
FIG. 3: Performance of ADHa deletion strain 3416, ADHb deletion strain 3859, ADHa/ADHb deletion strain 3860, and parent strain 3356 in defined media with 20 g/L dextrose and 80 g/L xylose at pH 4.8.
Figure 4:
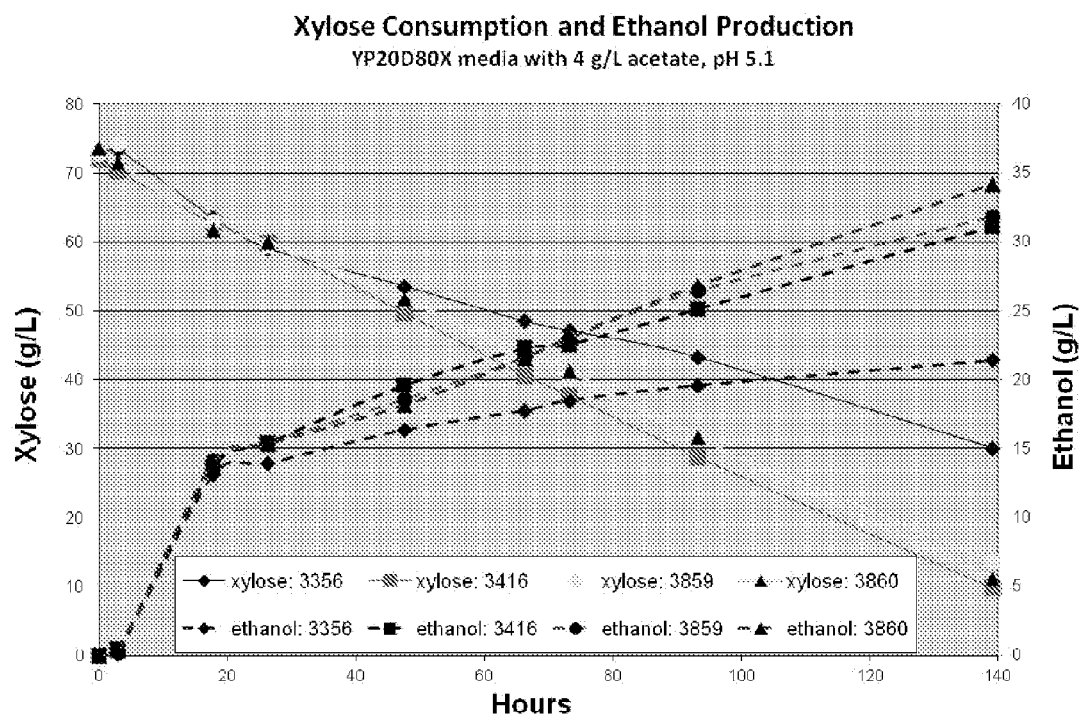
FIG. 4: Performance of ADHa deletion strain 3416, ADHb deletion strain 3859, ADHa/ADHb deletion strain 3860, and parent strain 3356 in defined media with 20 g/L dextrose and 80 g/L xylose at pH 5.1.

Two different ADHb knockout strains were generated using methods similar to those described above for ADHa. The first strain (3859) contained a double-knockout of ADHb, while the second strain (3860) contained a double-knockout of both ADHb and ADHa. Shake flask fermentations showed that strains 3859 and 3860 both exhibited improved xylose utilization and ethanol titer in YP 20D:80X media (YP-based media containing 20 g/L dextrose and 80 g/L xylose) at a pH of 4.8 versus parent strain 3356 and ADHa knockout strain 3416 (discussed below) (FIG. 3). Both strains also exhibited improved xylose utilization and ethanol titer in YP 20D:80X media that contained acetate at a pH of 5.1 (FIG. 4). All dextrose was consumed in these experiments by the 19 hour timepoint. These results establish that ADHa and ADHb knockout strains are capable of fermenting xylose to ethanol in both the presence and absence of acetate.

Example 4

Generation of Additional ADHa Knockout Strains

Three additional genetically modified *I. orientalis* strains were developed in which the gene encoding ADHa was knocked out.

The first ADHa knockout strain (strain 3416) contained four copies of an exogenous gene encoding *B. thetaiotaomicron* XI, two copies of a native exogenous gene encoding XK, and a full complement of native exogenous PPP enzymes (two copies each of TAL, TKL, RKI, and RPE. Strain 3416 expressed normal levels of endogenous ADH1.

The other two ADHa knockout strains (strains 3489 and 3490) were generated by integrating two extra copies of an ADH1 gene comprising the coding region set forth in SEQ ID NO:5 under the control of the strong glycolytic promoter TDH3 (glyceraldehyde 3-phosphate dehydrogenase) into the genome of strain 3416. The *I. orientalis* ADH1 gene sequence identified in Example 1 was amplified from genomic DNA using Pfu DNA polymerase and primers incorporating a XbaI restriction site on the 5' end and a PacI site on the 3' end. The resultant gel purified fragment was digested with PacI and XbaI and ligated into similarly digested vector pHJJ7. pHJJ7 contains an insert with the *I. orientalis* TDH3 promoter, *B. thetaiotaomicron* XI, *I. orientalis* PDC terminator, and an *I. orientalis* URA3 marker cassette ($P_{TDH3}$-BtXI-$T_{PDC}$-URA3), with the XI gene being released with the PacI/XbaI digest. Thus, ligation resulted in the ADH1 gene linked to the TDH3 promoter and a URA3 marker. The resultant vector (pHJJ60) was digested with NotI and the fragment containing the $P_{TDH3}$-ADH1-$T_{PDC}$-URA3 insert was gel purified. A gene (S141G8160) homologous to an *A. monospora* L-xylulose reductase gene was identified in *I. orientalis*. The enzyme encoded by this gene has been found to be active in the production of D-xylulose from D-arabitol in a non-pentose fermenting *I. orientalis* strain. Deletion of this gene may be useful in reducing xylitol formation from D-xylulose via xylitol dehydrogenase activity, thus making S141G8160 a beneficial insertion site. The regions upstream and downstream of S141G8160 were amplified using separate primer sets, and the resultant fragments were inserted into vector PCR2.1-TOPO with a NotI site between the fragments. This construct was transformed into E. coli, and colonies having plasmids with the desired inserts were identified by PCR. One insert was identified that did not have any sequence errors, and the vector with this insert was termed pHJJ63. pHJJ63 was digested with NotI, and the $P_{TDH3}$-ADH1-$T_{PDC}$-URA3 insert was ligated into NotI site. The ligation was transformed into E. coli and colonies were identified that contained plasmids with the insert in either orientation 1 (pHJJ61) or orientation 2 (pHJJ62).

The integration fragments from pHJJ61 and pHJJ62 ($P_{TDH3}$-ADH1-$T_{PDC}$-URA3 with S141G8160 flanks) were released by restriction digest. Linearized DNA from pHJJ61 was transformed into yACN77, the ura-derivative of strain 3416. Single colonies having integration at the S141G8160 site were confirmed by PCR. Two strains containing one copy of the ADH1 integration fragment were identified (strains yHJJ76 and yHJJ77). yHJJ76 was grown overnight in YPD media and plated onto ScD-FOA media to select for loss of the URA3 gene. Single colonies were purified on YPD and patched to ScD-ura and YPD media to confirm the ura-phenotype. Ura-colonies that had retained the integrated copy of ADH1 were identified by PCR. These ura-derivatives of yHJJ76 were named yHJJ80 and yHJJ81. Linearized DNA from pHJJ62 was transformed into pHJJ81, and single colonies were purified on ScD-ura media. Strains 3489 and 3490 were each confirmed by PCR to contain two copies of the ADH1 integration fragment at the S141G160 site.

Two additional strains were constructed that contained an ADHb deletion. For the first strain, two copies of the ADHb deletion vector were integrated, as previously described, into the ura-derivative of strain 4138, an ethanol tolerant mutant of strain 3489 derived by chemical mutagenesis and selection. This new strain was called strain 12053. For the second strain, two copies of the ADHb deletion vector were integrated, as previously described, into the ura-derivative of strain 3489. The resultant strain was named strain 3922.

The various ADH1 overexpression and/or ADHa/b deletion strains generated in this and previously examples are summarized in Table 4 (single copy and ura-derivatives not included).

TABLE 4

I. orientalis strains

| Strain name | Description | Parent strain |
|---|---|---|
| 3082 | Parent strain with exogenous XI, XK, and TAL genes, XR and XDH deletions | |
| 3085 | ADHa deletion | 3082 |
| 3356 | Parent strain with exogenous XI, XK, TAL, TKL, RKI, and RPI genes, XR and XDH deletions | |
| 3416 | ADHa deletion | 3356 |
| 3489, 3490 | ADHa deletion ADH1 overexpression S141G8160 deletion | 3416 |
| 3859 | ADHb deletion | 3356 |
| 3860 | ADHa deletion ADHb deletion | 3416 |
| 3863 | ADHa deletion S141G8160 deletion | 3416 |

TABLE 4-continued

I. orientalis strains

| Strain name | Description | Parent strain |
|---|---|---|
| 3922 | ADHa deletion ADHb deletion ADH1 overexpression S141G8160 deletion | 3489 |
| 4138 | Ethanol tolerant strain ADHa deletion ADH1 overexpression S141G8160 deletion | 3489 |
| 12053 | Ethanol tolerant strain ADHa deletion ADHb deletion ADH1 overexpression S141G8160 deletion | 4138 |

Example 5

Xylose Utilization and Ethanol Titer by ADHa Knockout Strains in Synthetic Media Three of the ADHa knockout strains generated in Example 4 (strains 3416, 3489, and 3490) were tested for their ability to produce ethanol from a mixed sugar YP-based media in shake flask fermentations. All three strains were grown overnight in YPD media in Falcon tubes, and these cultures were used to inoculate 50 mL of media in 125 mL baffled flasks to a starting $OD_{600}$ of 0.2. The shake flask media contained 20 g/L dextrose and 80 g/L xylose, pH 4.8. Flasks were incubated at 40° C. and 100 rpm. Samples were taken for HPLC analysis after 0, 8, 23, 32, 47, and 57 hours. 500 µl of sample was acidified with 50 µl of sulfuric acid, centrifuged, and the supernatant filtered. The pH and $OD_{600}$ of each sample were also taken.

Figure 5:
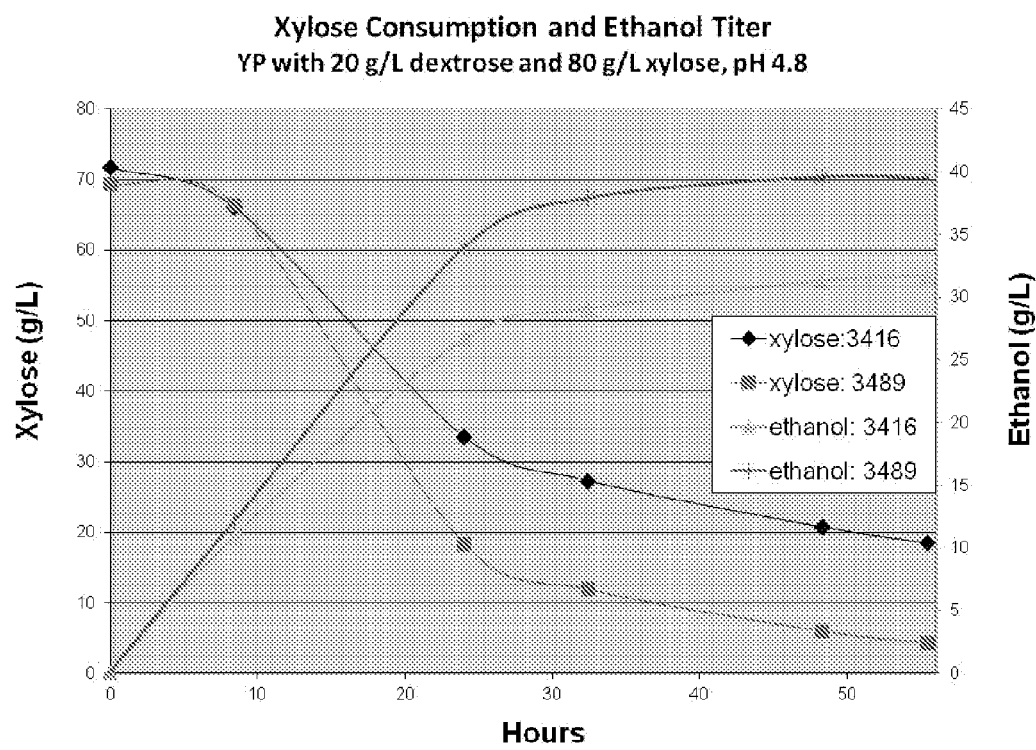
FIG. 5: Performance of ADHa deletion strain 3416 and ADH1 overexpression/ADHa deletion strain 3489 in defined media with 20 g/L dextrose and 80 g/L xylose at pH 4.8.

All three strains consumed all dextrose by the 9 hour timepoint, had similar growth rates, and exhibited the ability to ferment xylose to ethanol. However, the two strains that overexpressed ADH1 (strains 3489 and 3490) exhibited 25% greater xylose utilization and 23% greater ethanol titer than the parent strain that did not overexpress ADH1 (strain 3416) (FIG. 5). In addition, the ADH1 overexpressing strains produced slightly more arabitol and glycerol and slightly less xylitol than the parent strain.

Example 6

Xylose Utilization and Ethanol Titer by ADHa Knockout Strains in Hydrolysate Media Three of the ADHa knockout strains from Example 4 (strains 3416, 3489, and 3490) were next tested for their ability to produce ethanol in various hydrolysate media. Loops of biomass from YPD plates were used to inoculate 250 mL baffled flasks containing 100 mL defined media (DMDX) or YP-based media (YPDX) having 20 g/L dextrose and 80 g/L xylose and pH adjusted to around 5.0. The defined media contained urea as a nitrogen source and 0.2M MES buffer. The cells were incubated at 250 rpm and 37° C. for 15-24 hours, and harvested in mid-late exponential growth phase. Cultures were mixed with 80% glycerol stock and separated into 1 mL aliquots. 50 to 400 µl from each aliquot was transferred to 100 mL of media in a 250 mL shake flask, incubated at 250 rpm and 37° C. for 15-24 hours, and harvested in mid-late exponential growth. 35 to 40 mL samples were harvested and inoculated into batch fermentation vessels containing various hydrolysate media.

Samples were harvested at 4 to 8 hour intervals throughout the fermentation and tested for $OD_{600}$ using a spectrophotometer and for substrates and product levels using HPLC analyses.

Figure 6:
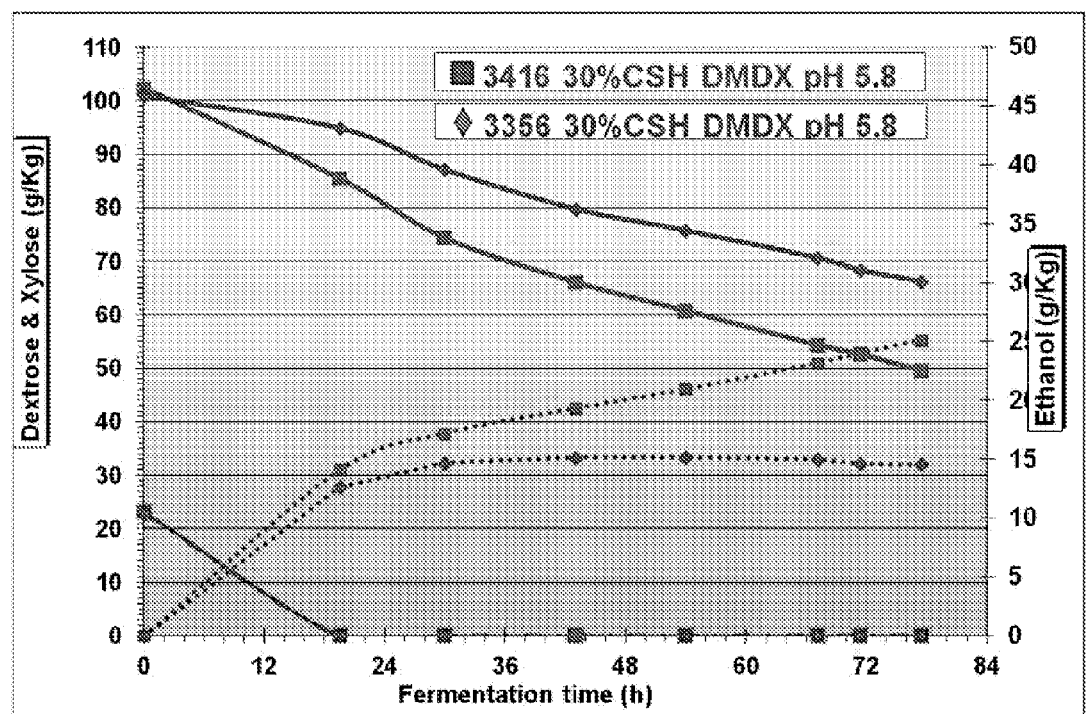
FIG. 6: Performance of ADHa deletion strain 3416 and parent strain 3356 in 30% CSH DMDX medium at pH 5.8.

The ADHa knockout strain 3416 exhibited a 60% increase in ethanol titer and a 50% increase in xylose consumption versus parent strain 3356 in a 30% corn stover hydrolysate (CSH) DMDX media at pH 5.8 (FIG. 6). These results confirm that knocking out ADHa expression increases ethanol titer in *I. orientalis*.

Figure 7:
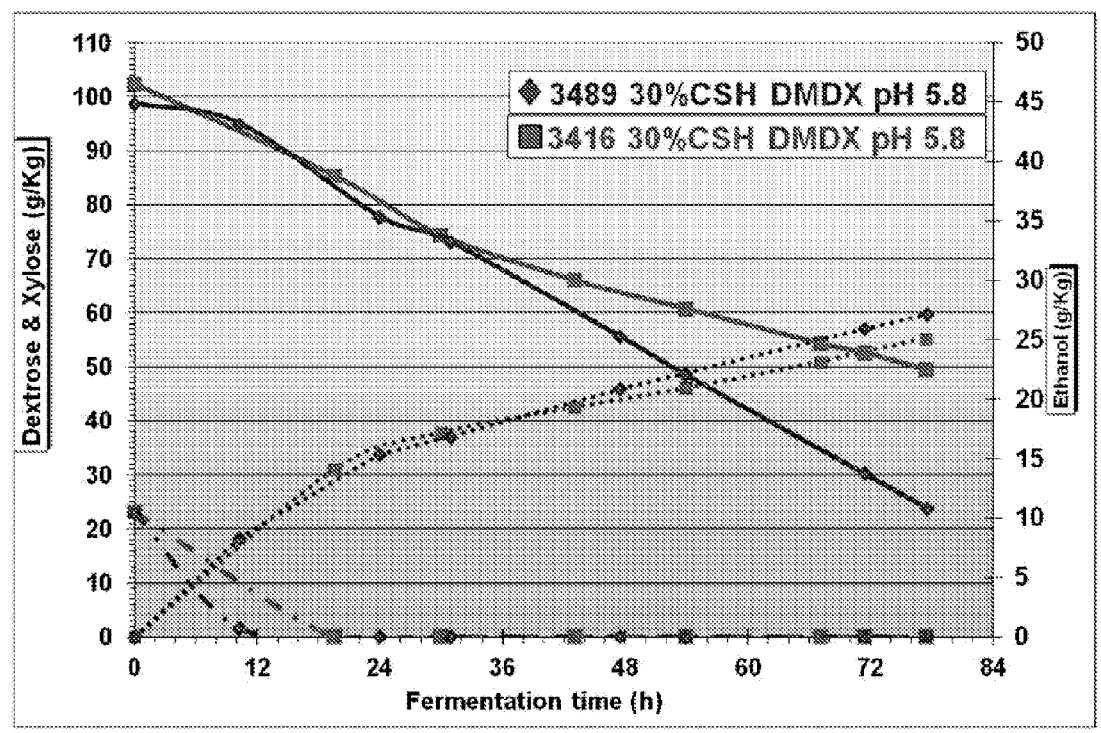
FIG. 7: Performance of ADHa deletion strain 3416 and ADH1 overexpression/ADHa deletion strain 3489 in 30% CSH DMDX medium at pH 5.8.

The increase in ethanol titer and xylose consumption was even greater in the ADHa knockout strain that overexpressed ADH1. Strain 3489 exhibited approximately a 40% increase in xylose utilization and a 10% increase in ethanol titer versus strain 3416 in the 30% CSH DMDX media at pH 5.8 (FIG. 7). The difference in ethanol titer between strains 3416 and 3489 was even more marked (30% increase) in a 15% hydrolysate medium (15% CSH 5 g/L acetic acid DMDX) at pH 4.9. In YP 20D:80X media at pH 4.9, the ADH1 overexpressing strain showed a 10% increase in ethanol titer.

Example 7

Figure 8A:
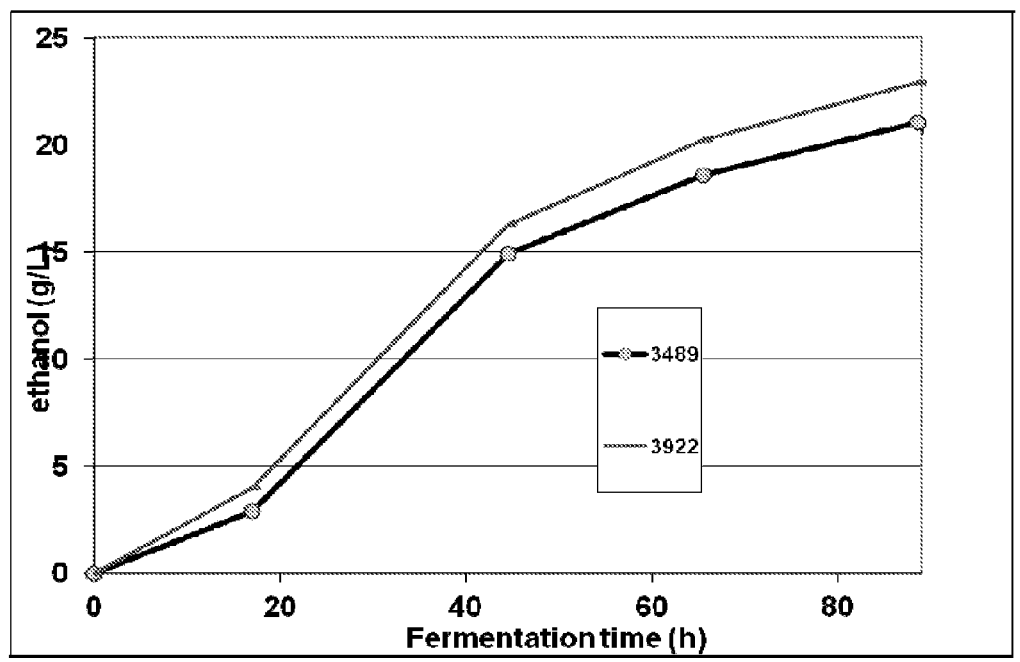
FIG. 8: Performance of ADH1 overexpression/ADHa deletion strains 3489 and 4138 and ADH1 overexpression/ADHa/ADHb deletion strains 3922 and 12053 in CSH medium at pH 5.0.
Figure 8B:
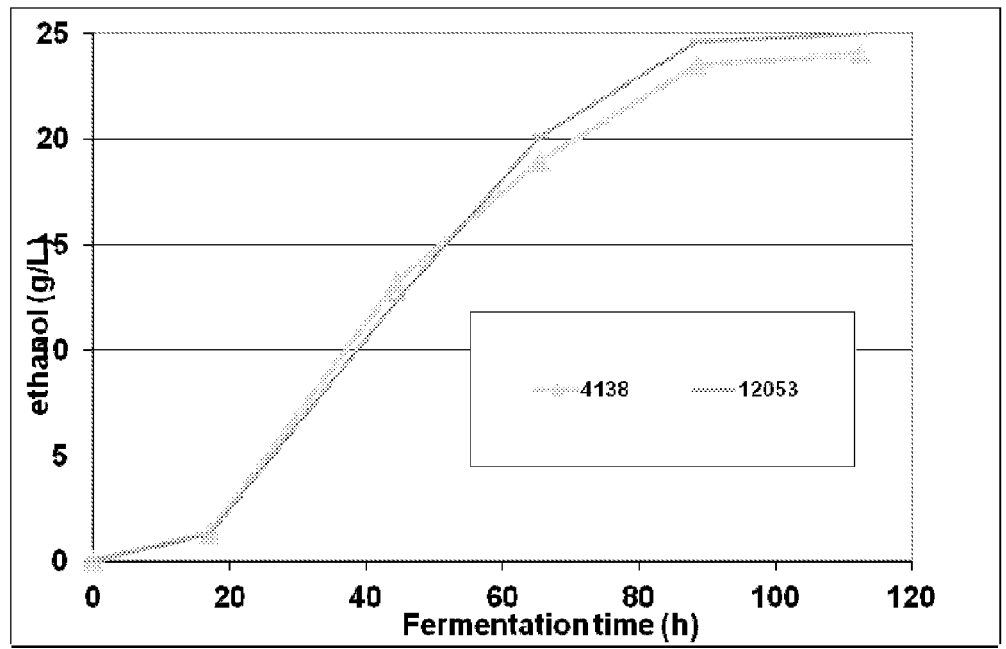

Xylose Utilization and Ethanol Titer by ADHb Knockout Strains in Hydrolysate Media The ADHb knockout strains from Example 4 (strains 3922 and 12053), as well as ADHa knockout strains 3489 and 4138, were tested for their ability to produce ethanol in a liquefied corn stover hydrolysate medium. This medium contained 20% solids with a defined media base at pH 5.0. The hydrolysate was treated with cellulase (15 mg/g glucan) for 6 hours at 50° C. prior to use in fermentation. Starting sugars levels in the media were 13 g/L glucose and 24 g/L xylose. Shake flasks were run at 100 rpm and 37° C., and lime was used for pH adjustment. Deletion of ADHb provided a modest but consistent increase in ethanol titer under these conditions (FIG. 8).

Example 8

Incorporation of Additional Copies of the ADH1 Gene

One or more of the genetically modified *I. orientalis* strains disclosed in the above examples will be further genetically modified by incorporating additional copies of the ADH1 gene. The resultant strains may contain three, four, or more copies of ADH1 gene, one or more of which may be connected to a strong promoter.

ADHa and/or ADHb knockout strains containing three exogenous copies of the ADH1 gene linked to a strong promoter will be generated. The ability of these strains to ferment xylose to ethanol will be tested in various media, including both synthetic media and CSH media. It is expected that these strains will exhibit xylose utilization and ethanol titer that are the same as or better than corresponding strains containing two exogenous copies of the ADH1 gene.

Example 9

Overexpression of ADH1 in the Absence of ADHa/ADHb Knockout

A genetically modified *I. orientalis* strain will be developed that comprises intact copies of both the ADHa and ADHb genes, but which overexpresses ADH1. The resultant yeast strain will be tested for its ability to ferment xylose-containing medium to ethanol, and is expected to show increased xylose consumption and ethanol titer versus a parent strain that does not overexpress ADH1. This strain is also expected to support the additive effect of ADH1 overexpression and AHD2a/ADHb deletion.

Example 10

Incorporation of Additional Genetic Modifications into ADHa/ADHb Knockout and ADH1 Overexpressing Yeast Strains One or more additional genetic modifications will be incorporated into one or more of the genetically modified yeast strains described in the previous examples. These additional genetic modifications may include introduction of one or more exogenous arabinose pathway genes or sugar transporter genes, or deletion or disruption of one or more genes encoding enzymes involved in non-preferred fermentation pathways or by-product production. The resultant yeast strains will be tested for their ability to ferment xylose-containing medium to ethanol, and it is expected that one or more of these strains may exhibit improved xylose consumption and ethanol titer versus their parental strains.

Example 11

Testing of Genetically Modified *I. orientalis* in Various Media

Certain of the genetically modified yeast strains described in the previous examples were tested for their ability to ferment xylose to ethanol in mixed sugar media in laboratory scale fermentors. Characterization was performed in a 2-L single-stage batch-culture reactor containing 1.5 L of a defined medium. Media for both protocols contained carbon sources in the form of 20 g/L dextrose, 80 g/L xylose, and 10 g/L arabinose, as well as 10 g/L glacial acetic acid. Salts were added in the form of 3.0 g/L potassium phosphate monobasic and 0.5 g/L magnesium sulfate heptahydrate. Stock solutions of salts, trace minerals, vitamins, and defoaming agent were prepared and filter sterilized separately. The sugars and water were autoclaved in the fermentation vessel, with all other components added aseptically to the medium post-sterilization. The first batch protocol was run at pH 4.95. The batch medium was neutralized prior to inoculation and maintained at the target pH using 2M sulfuric acid and 15% lime. This batch medium contained 2.25 g/L urea salt as the nitrogen source. The second batch protocol was neutralized to pH 5.8 with 2 g 15% lime and 15% ammonia hydroxide, with the latter also serving as the nitrogen source.

Other fermentation conditions were consistent for both protocols. Temperature was maintained at 37° C., and aeration for a target oxygen uptake rate (OUR) of 5 mmol/L/h was achieved by sparging air through the batch medium at a flow rate of 0.25 slpm and a constant agitation speed of 450 rpm. Oxygen levels were monitored using an in-vessel $O_2$ electrode. Each prepared batch-culture reactor was inoculated to target cell density of 0.15 g/L dry cell weight with up to 50 mL of an overnight culture grown in like medium. Samples were taken for HPLC analysis at the start of the fermentation and one or two times per day thereafter.

Figure 9A:
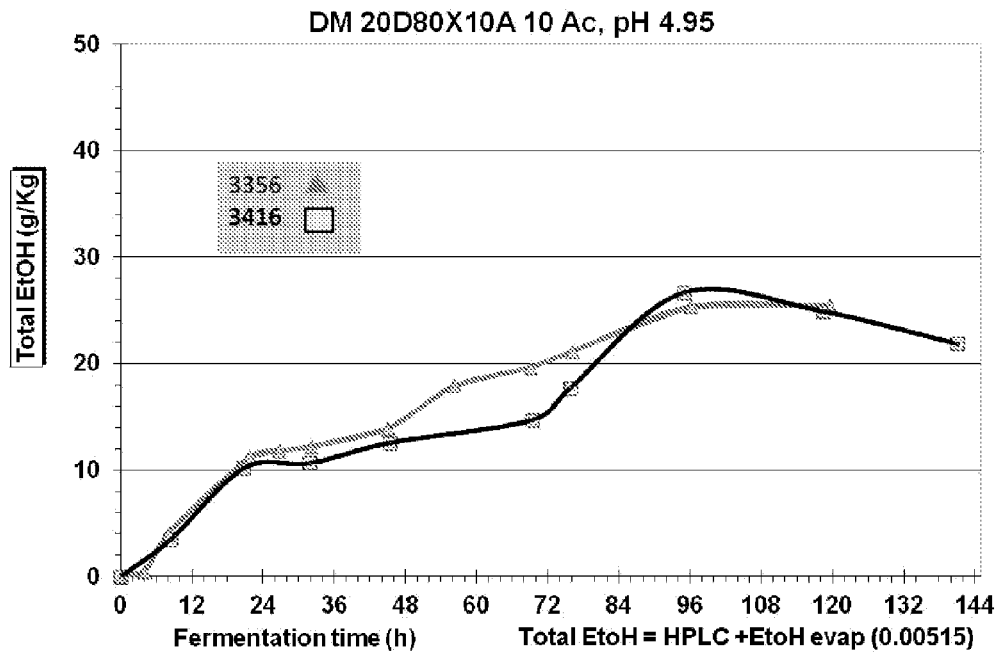
FIG. 9: Performance of ADHa deletion strain 3416 and its parent strain 3356 in defined media with 20 g/L dextrose, 80 g/L xylose, 10 g/L arabinose, and 10 g/L acetate at pH 4.95.
Figure 9B:
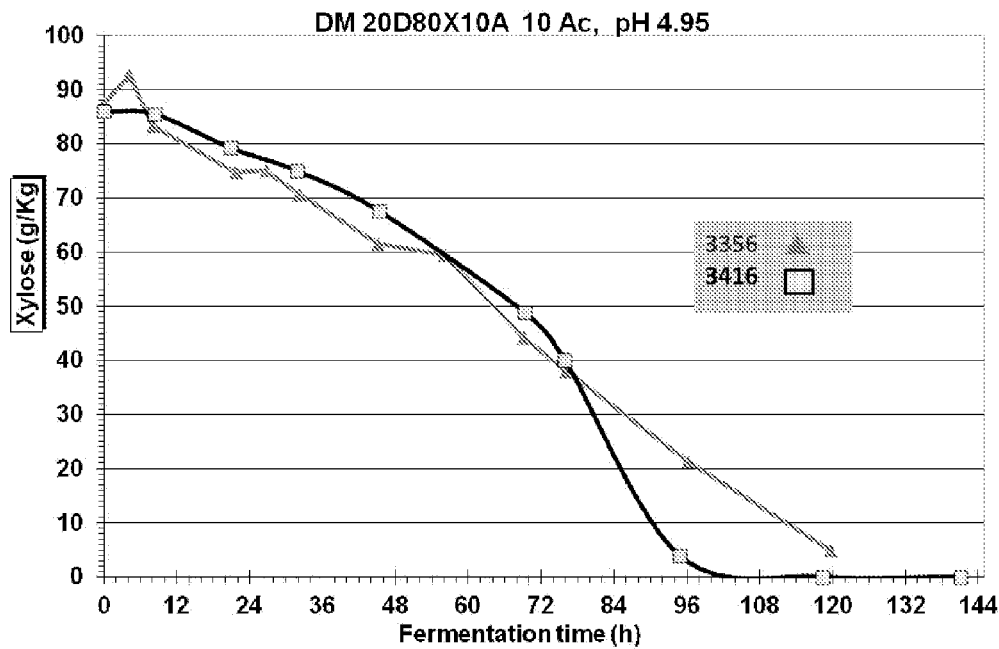
Figure 10A:
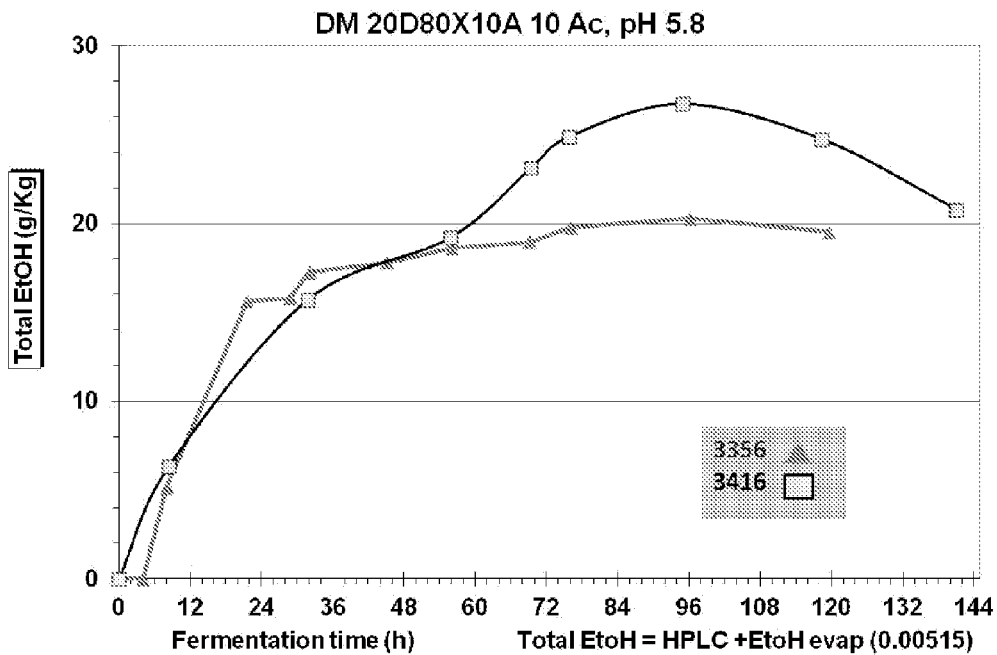
FIG. 10: Performance of ADHa deletion strain 3416 and its parent strain 3356 in defined media with 20 g/L dextrose, 80 g/L xylose, 10 g/L arabinose, and 10 g/L acetate at pH 5.8.
Figure 10B:
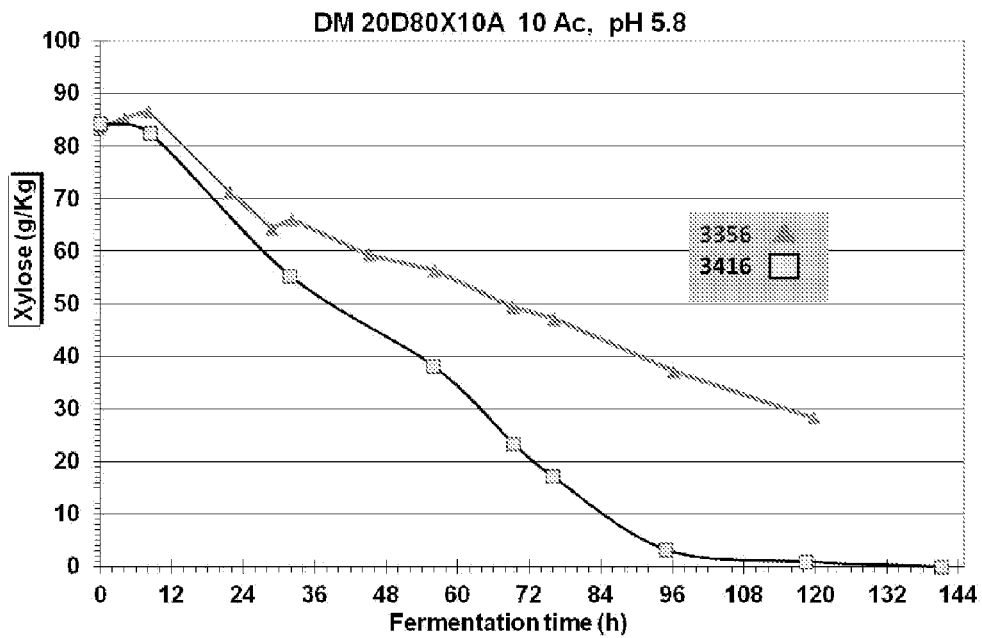
Figure 11A:
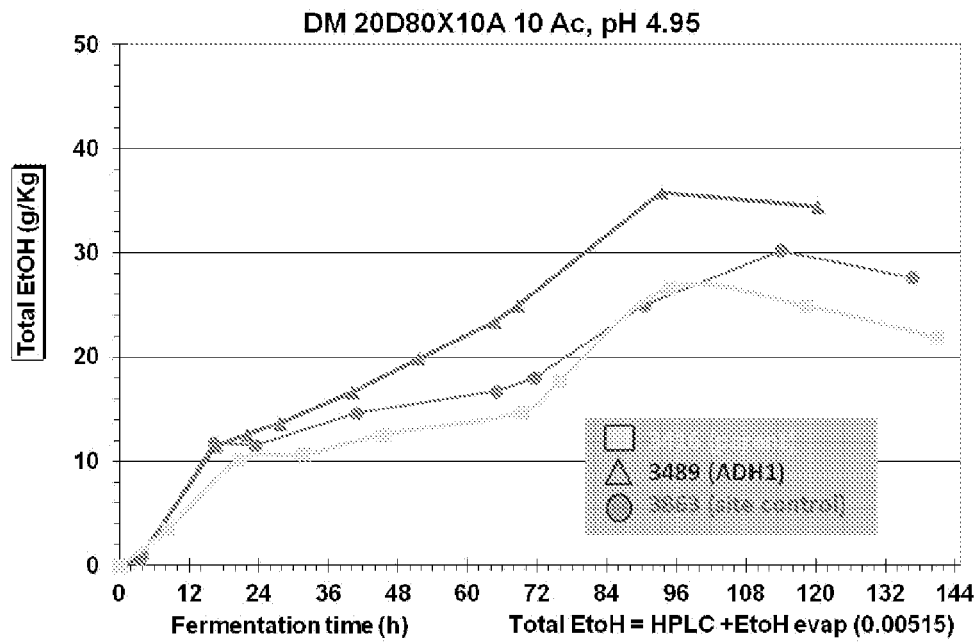
FIG. 11: Performance of ADH1 overexpression/ADHa deletion strain 3489, its parent ADHa deletion strain 3416, and insertion site control strain 3863 in defined media with 20 g/L dextrose, 80 g/L xylose, 10 g/L arabinose, and 10 g/L acetate at pH 4.95.
Figure 11B:
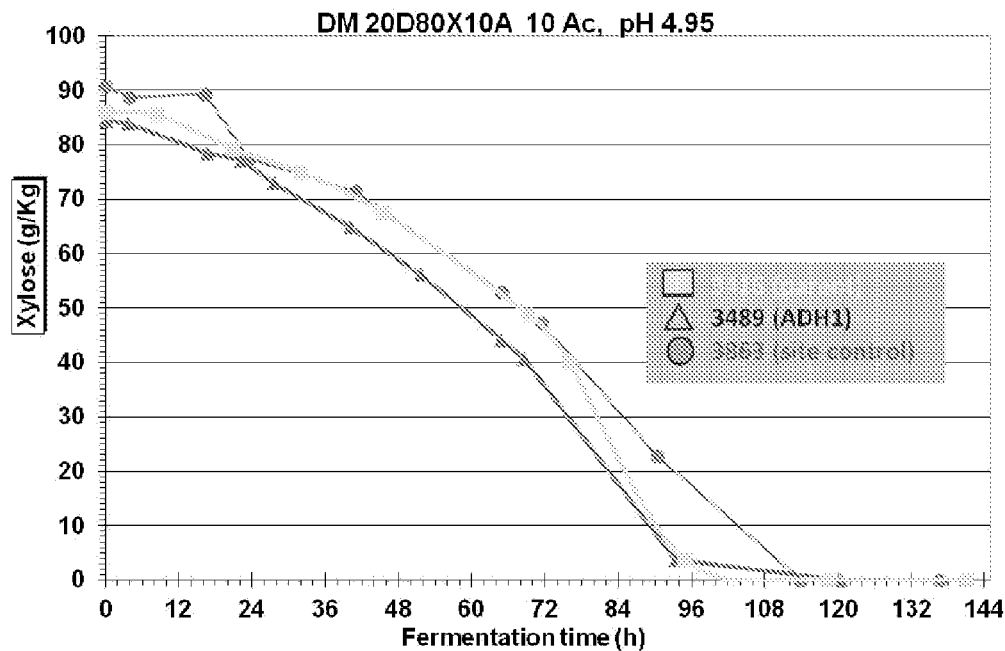
Figure 12A:
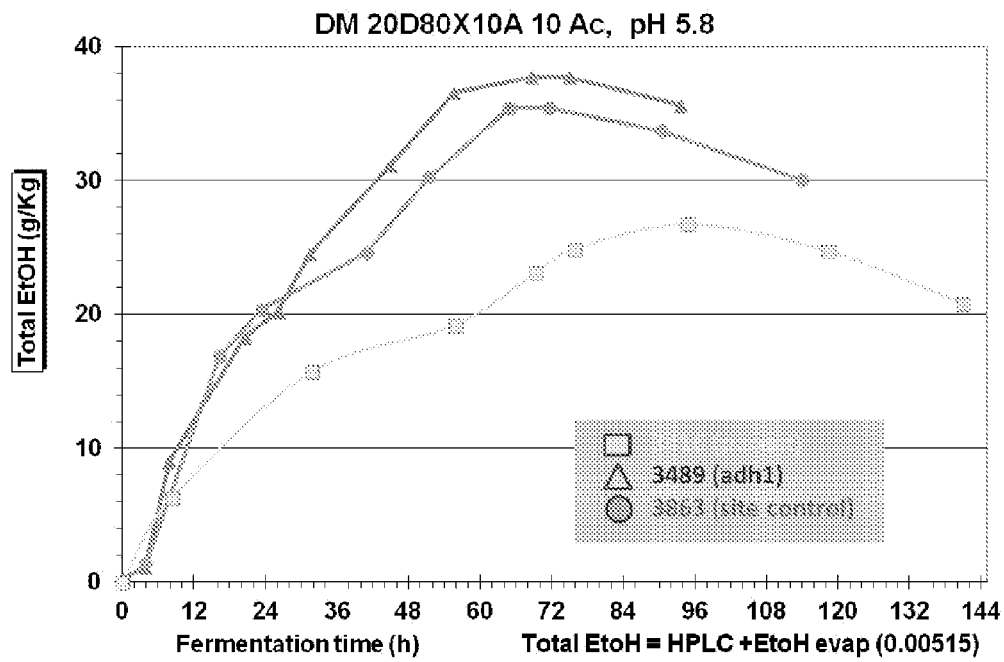
FIG. 12: Performance of ADH1 overexpression/ADHa deletion strain 3489, its parent strain ADHa deletion strain 3416, and insertion site control strain 3863 in defined media with 20 g/L dextrose, 80 g/L xylose, 10 g/L arabinose, and 10 g/L acetate at pH 5.8.
Figure 12B:
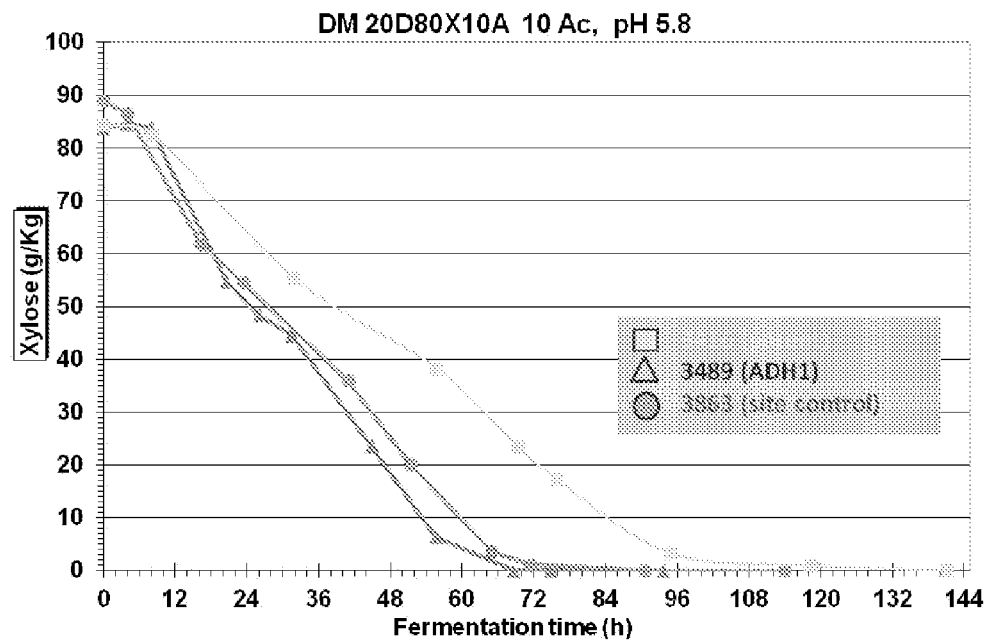
Figure 13A:
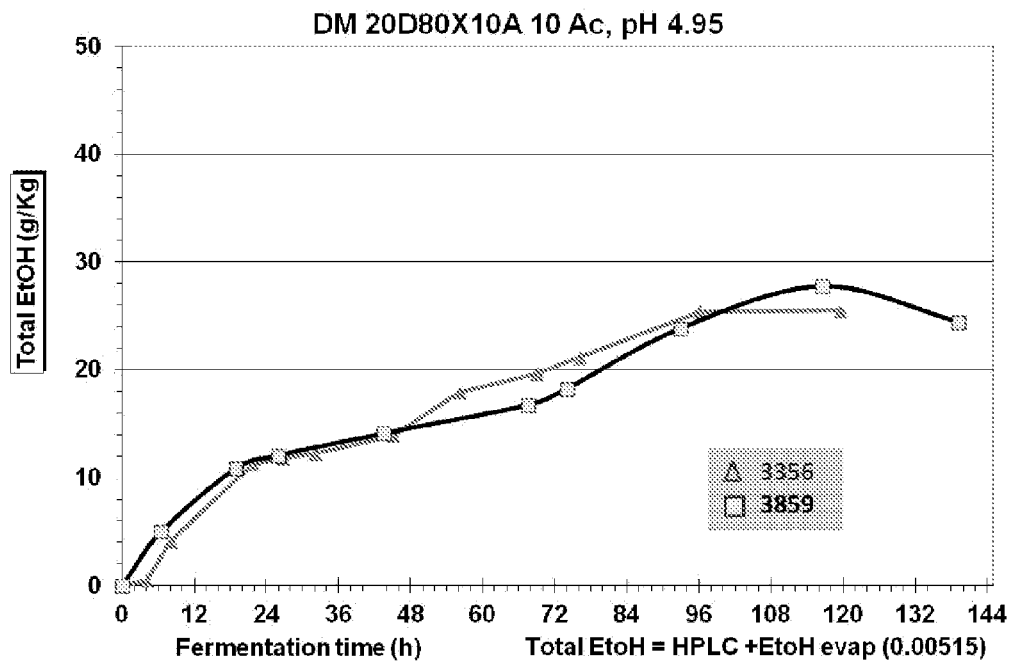
FIG. 13: Performance of ADHb deletion strain 3859 and its parent strain 3356 in defined media with 20 g/L dextrose, 80 g/L xylose, 10 g/L arabinose, and 10 g/L acetate at pH 4.95.
Figure 13B:
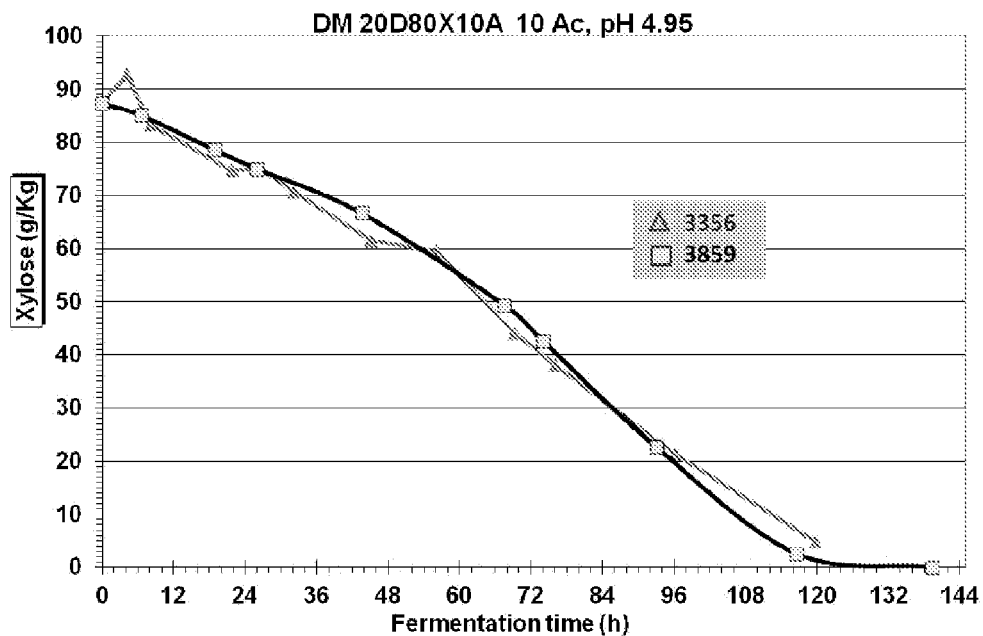
Figure 14A:
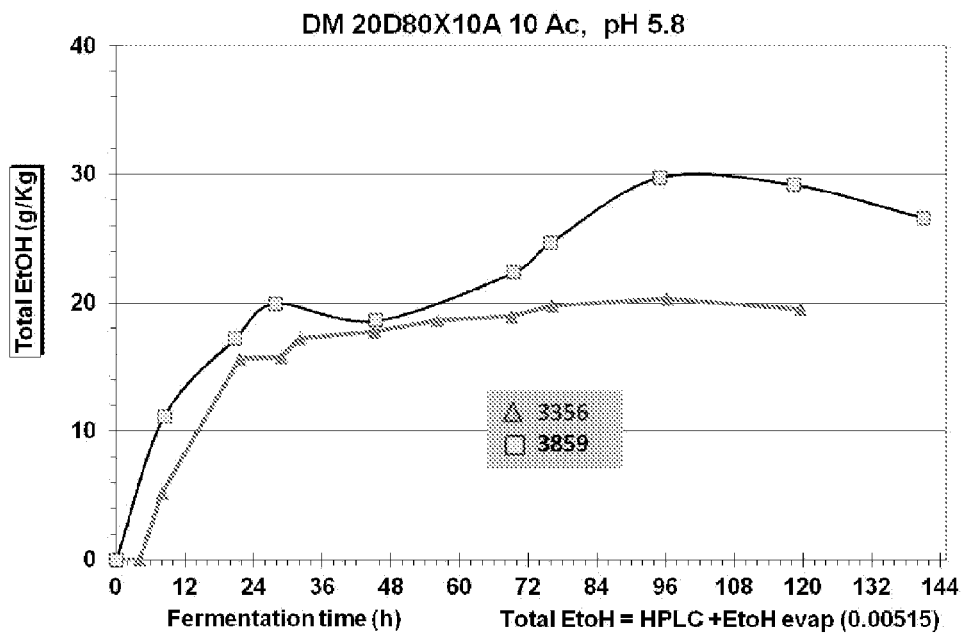
FIG. 14: Performance of ADHb deletion strain 3859 and its parent strain 3356 in defined media with 20 g/L dextrose, 80 g/L xylose, 10 g/L arabinose, and 10 g/L acetate at pH 5.8.
Figure 14B:
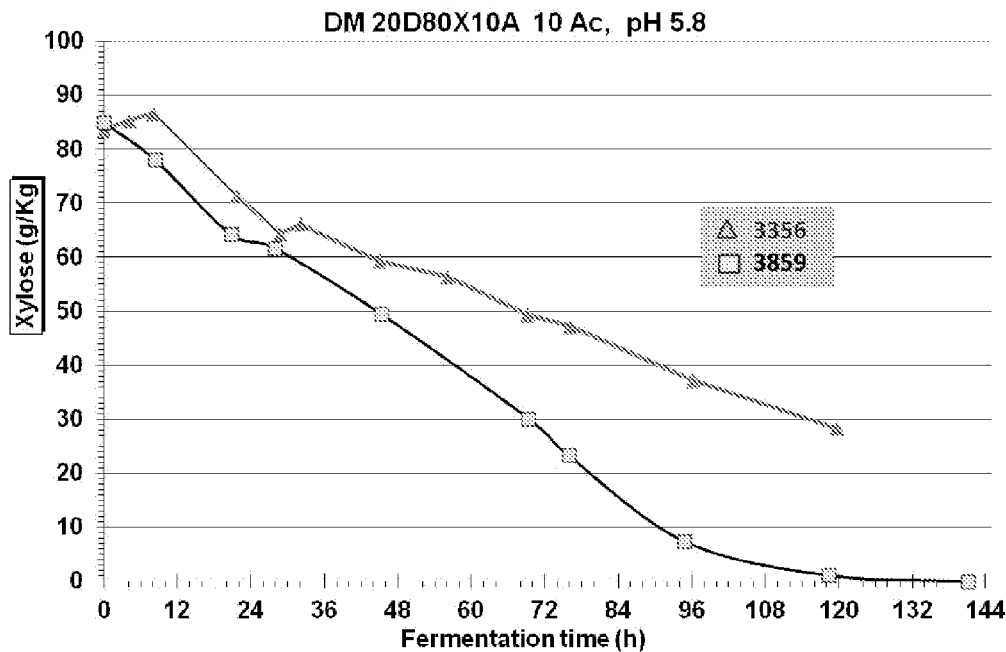

The effects of the gene modifications in these strains varied with the media used (see FIGS. 9-14). In all cases, dextrose was consumed in approximately 24 hours. Both deletion strains (3416 and 3859) showed a significant increase in ethanol titer and xylose utilization in the pH 5.8 fermentations relative to their parent strains (FIGS. 10 and 14). For the ADHa deletion strain (3416), a benefit of the deletion was also seen for xylose utilization late in the pH 4.95 fermentation (FIG. 9). The ADHa deletion/ADH1 overexpression strain (3489), on the other hand, showed a significant benefit on both xylose consumption and ethanol titer in the pH 4.95 fermentation (FIG. 11) relative to its parent strain 3416. Strain 3489 also performed much better than its parental strain at the higher pH. However, much of this benefit appears to be attributable to the insertion site deletion, as shown by the improved performance of the insertion site control strain 3863 (FIG. 12). Strains having the S141G8160 deletion (3489 and 3863) exhibited lower xylitol production with both fermentation media. In the pH 4.95 medium, the xylitol levels at 114 hours were 3.2, 2.7, and 2.4 g/L for strains 3416, 3863, and 3489, respectively. For the pH 5.8 medium, the respective values at 94 hours were 2.4, 1.8, and 1.5 g/L.

Example 12

Overexpression of Other Exogenous ADH1 Genes in *I. orientalis*

Strains over-expressing alternative sources of an ADH1 gene linked to a strong promoter will be generated. The ability of these strains to ferment xylose to ethanol will be tested in various media, including both synthetic media and CSH media. It is expected that these ADH1 strains may exhibit xylose utilization and ethanol titer that is higher than that of parental strains. Sources of the ADH1 gene may include *S. cerevisiae, P. stipitis, K. lactis*, and/or *C. maltosa*.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein.

What is claimed is:

1. A genetically modified yeast cell that overexpresses a first polypeptide comprising an amino acid sequence with at least 90% sequence identity to the amino acid sequence set forth in SEQ ID NO:6 and comprises a deletion or disruption of a gene encoding a second polypeptide comprising an amino acid sequence with at least 90% sequence identity to an amino acid sequence selected from the group consisting of the amino acid sequences set forth in SEQ ID NO:2 and SEQ ID NO:4.

2. The genetically modified yeast cell of claim 1, wherein the polypeptide comprising an amino acid sequence with at least 90% sequence identity to the amino acid sequence set forth in SEQ ID NO: 6 is capable of catalyzing the conversion of acetaldehyde to ethanol.

3. The genetically modified yeast cell of claim 1, wherein said first polypeptide comprises the amino acid sequence set forth in SEQ ID NO:6.

4. The genetically modified yeast cell of claim 1, wherein said second polypeptide comprises an amino acid sequence selected from the group consisting of the amino acid sequences set forth in SEQ ID NO:2 and SEQ ID NO:4.

5. The genetically modified yeast cell of claim 1, wherein said yeast cell belongs to the *I. orientalis/P. fermentans* clade.

6. The genetically modified yeast cell of claim 5, wherein said yeast cell is *I. orientalis*.

7. A fermentation process wherein a genetically modified yeast cell as recited in claim 1 is cultured in fermentation media comprising xylose.

8. The fermentation process of claim 7, wherein said fermentation media comprises at least 10 g/L xylose from a plant biomass hydrolysate.

9. The fermentation process of claim 8, wherein xylose is the most abundant sugar in said fermentation media.

10. A fermentation process as recited in claim 7, wherein ethanol is produced.

11. The process of claim 10, wherein said xylose-containing media comprises at least 10 g/L xylose from a plant biomass hydrolysate.

12. The method of claim 11, wherein xylose is the most abundant sugar in said media.

\* \* \* \* \*

SEQUENCE LISTING

```
<160> NUMBER OF SEQ ID NOS: 15

<210> SEQ ID NO 1
<211> LENGTH: 3179
<212> TYPE: DNA
<213> ORGANISM: Issatchenkia orientalis
<220> FEATURE:
<221> NAME/KEY: CDS
<222> LOCATION: (1052)..(2182)

<400> SEQUENCE: 1
gatttggacc tacaaggtgc tgtaaagagt atgaacactt ctggggagga ggaatggaac      60
agtgatgacg atgatgatga agaaagtgac gaaagtaacg aaagtgatta ctattcttac     120
gatgaaggcg aagaaacaga tgatagtgag ggagcccaag agggagagga agacgaaaat     180
gaacgaatca ttgaagctct aagtagtggt gttggtgaac tcaagatgga ctctttaggt     240
aattatattc ttgaatagtt gtgtaaagcg aatatgcaaa tagatttgtt ttataattat     300
gcatctcttt gaaagaggtt tagaggcaaa gttcttgcat acaatattgt gattgtttta     360
atgtcattct tgattttcat aaagagatta aaaaaaaaa aaaaaaactt ataaaattga     420
gtagaaccat ttatatataa gacaaagatt gtctgtatta gtcctcaaca cactaaacct     480
tacatactta gggtaaattt gctaatagag tgatatgttc atgagaactc caacgacaac     540
acaaccacct atttgcacaa caaacaccat tgtcgcacgc tgcgcgccct agaagtagaa     600
agaaagggaa atgacattaa gagaatcata ccccgtgccc gtaacgccga aaaatcaca      660 ccccgtcccc cacaccttaa aacctcaacc gcttaacacc gccacaccct ttctctttat     720
aaacgccgtt tgcattactc attcttctta taaaccgcac cccccaaaac gcggaatagc     780
ttcaaccccc caatcagata tgagtttccc gggaaacccg cttttcccga cagccccaca     840
aggggttggt ctataaaaga ggacgttttc cccgtcatcg agattgaaga ttcttacagg     900
cccatttatt caaattggag ttgattcttc ttgtctttac tttctttctc tctttttctt     960 cctttttaa  tattatcttt tgtcaagcct ggttccctaa gttgaactct cttttcttgt    1020
gatcctccta tatagatacg ccttgccaaa t atg ttt gca tca acc ttc aga       1072
                                  Met Phe Ala Ser Thr Phe Arg
                                    1               5 agt caa gct gta aga gct gca aga ttt act aga ttc caa tcc act ttt      1120
```

|     |     |     |     |     |     |     |     |     |     |     |     |     |      |
|-----|-----|-----|-----|-----|-----|-----|-----|-----|-----|-----|-----|-----|------|
| Ser | Gln | Ala | Val | Arg | Ala | Ala | Arg | Phe | Thr | Arg | Phe | Gln | Ser | Thr | Phe |
|     | 10  |     |     |     |     | 15  |     |     |     |     | 20  |     |      |

```
gcc att cct gag aag caa atg ggt gtt atc ttt gaa act cat ggt ggt      1168
Ala Ile Pro Glu Lys Gln Met Gly Val Ile Phe Glu Thr His Gly Gly
25              30                  35 cct tta caa tac aag gaa att cca gtt cca aaa cca aaa cca act gaa      1216
Pro Leu Gln Tyr Lys Glu Ile Pro Val Pro Lys Pro Lys Pro Thr Glu
40              45                  50                  55 att tta atc aat gtt aaa tac tct ggt gtc tgc cat acc gat tta cac      1264
Ile Leu Ile Asn Val Lys Tyr Ser Gly Val Cys His Thr Asp Leu His
                60                  65                  70 gca tgg aaa ggt gac tgg cca tta cca gca aag tta ccc cta gtt ggt      1312
Ala Trp Lys Gly Asp Trp Pro Leu Pro Ala Lys Leu Pro Leu Val Gly
            75                  80                  85 ggt cac gaa ggt gcg ggc att gtt gtt gcg aaa ggt tct gca gtt acc      1360
Gly His Glu Gly Ala Gly Ile Val Val Ala Lys Gly Ser Ala Val Thr
        90                  95                  100 aac ttt gag att ggc gat tat gct ggt att aag tgg tta aac ggt tca      1408
Asn Phe Glu Ile Gly Asp Tyr Ala Gly Ile Lys Trp Leu Asn Gly Ser
    105                 110                 115 tgt atg tca tgt gaa ttc tgt gaa caa ggt gat gaa tct aac tgt gaa      1456
Cys Met Ser Cys Glu Phe Cys Glu Gln Gly Asp Glu Ser Asn Cys Glu
120                 125                 130                 135 cat gcc gat ttg agt ggt tat act cat gat ggt tct ttc caa caa tat      1504
His Ala Asp Leu Ser Gly Tyr Thr His Asp Gly Ser Phe Gln Gln Tyr
                140                 145                 150 gcc act gct gac gct att caa gct gca aag atc cca aag ggt acc gac      1552
Ala Thr Ala Asp Ala Ile Gln Ala Ala Lys Ile Pro Lys Gly Thr Asp
            155                 160                 165 tta tct gaa gtt gcg cca att tta tgt gct ggt gtt act gtc tat aaa      1600
Leu Ser Glu Val Ala Pro Ile Leu Cys Ala Gly Val Thr Val Tyr Lys
        170                 175                 180 gct ttg aaa act gct gat tta aga gca ggt caa tgg gtt gcg att tct      1648
Ala Leu Lys Thr Ala Asp Leu Arg Ala Gly Gln Trp Val Ala Ile Ser
    185                 190                 195 ggt gcc gct ggt ggt cta ggt tct ctt gct gtc caa tat gca aag gca      1696
Gly Ala Ala Gly Gly Leu Gly Ser Leu Ala Val Gln Tyr Ala Lys Ala
200                 205                 210                 215 atg ggt cta aga gtt tta ggt atc gat ggt ggt gaa ggt aaa aag gaa      1744
Met Gly Leu Arg Val Leu Gly Ile Asp Gly Gly Glu Gly Lys Lys Glu
                220                 225                 230 ctt ttt gaa caa tgt ggt ggt gat gtg ttt atc gat ttc acc aga tac      1792
Leu Phe Glu Gln Cys Gly Gly Asp Val Phe Ile Asp Phe Thr Arg Tyr
            235                 240                 245 cca aga gat gca cct gaa aag atg gtt gct gat att aag gct gca act      1840
Pro Arg Asp Ala Pro Glu Lys Met Val Ala Asp Ile Lys Ala Ala Thr
        250                 255                 260 aac ggt ttg ggt cca cac ggt gtt atc aat gtc tct gtc tcc cca gct      1888
Asn Gly Leu Gly Pro His Gly Val Ile Asn Val Ser Val Ser Pro Ala
    265                 270                 275 gct atc tct caa tca tgt gac tat gtt aga gca act ggt aag gtt gtc      1936
Ala Ile Ser Gln Ser Cys Asp Tyr Val Arg Ala Thr Gly Lys Val Val
280                 285                 290                 295 ctt gtc ggt atg cca tct ggt gct gtc tgt aag tct gat gtc ttc act      1984
Leu Val Gly Met Pro Ser Gly Ala Val Cys Lys Ser Asp Val Phe Thr
                300                 305                 310 cat gtt gtt aaa tcc tta caa att aaa ggt tct tat gtt ggt aac aga      2032
His Val Val Lys Ser Leu Gln Ile Lys Gly Ser Tyr Val Gly Asn Arg
            315                 320                 325
```

| | | |
|---|---|---|
| gca gat acc aga gaa gct ttg gaa ttc ttt aat gaa ggt aag gtc aga<br>Ala Asp Thr Arg Glu Ala Leu Glu Phe Phe Asn Glu Gly Lys Val Arg<br>330                         335                     340 | | 2080 |
| tct cca atc aag gtt gtc cca tta tct act tta cct gaa att tac gaa<br>Ser Pro Ile Lys Val Val Pro Leu Ser Thr Leu Pro Glu Ile Tyr Glu<br>     345                     350                     355 | | 2128 |
| ttg atg gag caa ggt aag att tta ggt aga tac gtt gtt gat act tct<br>Leu Met Glu Gln Gly Lys Ile Leu Gly Arg Tyr Val Val Asp Thr Ser<br>360                         365                     370                     375 | | 2176 |
| aaa taa tgaagatgaa gaaaacagca aactttttat gactacccccc aaccatctaa<br>Lys | | 2232 |
| cgatttatga tctatatata gctttctaga acatccattt atttattcac ttactcatgt | | 2292 |
| atttatatta tataatacaa ataactaat tacaatgtgt acatttttt ttttcattac | | 2352 |
| cataatgtat gcgttgagcc tcttgcacct tctttattag gaaatcagtt gaaaatttc | | 2412 |
| cggattgtct ttattattgg cccatttttt tttggtcaca cctttatttt tgtacacttc | | 2472 |
| tcgggcaaag caaaaactat agtaccggat aggcctttat aaaactccag tgtgtatgat | | 2532 |
| tttagttggt gtgccatcta cacgttctct tagtttcttt atcatgtcac agaaagcaag | | 2592 |
| catgcaaacc cttacaaaaa ataacaacat acaaatgcct aaacaactgg actataatga | | 2652 |
| tggtgagtca gttacgaaaa gagcaagtgg gttaatacga tttcgtaagg gacagtctga | | 2712 |
| ggaagactac aattttcaaa aggagcagtt ctggtccacg ggtcctttag tacagaatca | | 2772 |
| cacatttgtg actgaatttg ttgaaaagtt tattgaaaac acaattagtg aagattattc | | 2832 |
| aatcacagat agatcgaaaa tagaacgtga acaatcata cacggattgg agaagctgta | | 2892 |
| ttttcaaagg gaatatgagc gatgtctaaa agatgttcaa ctattgaagg acaatatcga | | 2952 |
| taagttcaat cctaatttgg atcttaatga aaagaattta taatgagctg aattatatt | | 3012 |
| cttggatgtg catcaaaaag atccatgaga gtaacgaaaa gaaactgggg gaaatctaat | | 3072 |
| aatttcaat ttcaatatac acttctatat cctttaatgt aatggcttta taaataaaca | | 3132 |
| cgaacttcta cagcaccgac gtttcttttt cttaccagct cctcttc | | 3179 |

<210> SEQ ID NO 2
<211> LENGTH: 376
<212> TYPE: PRT
<213> ORGANISM: Issatchenkia orientalis

<400> SEQUENCE: 2

Met Phe Ala Ser Thr Phe Arg Ser Gln Ala Val Arg Ala Ala Arg Phe
1                 5                    10                 15

Thr Arg Phe Gln Ser Thr Phe Ala Ile Pro Glu Lys Gln Met Gly Val
                 20                    25                    30

Ile Phe Glu Thr His Gly Gly Pro Leu Gln Tyr Lys Glu Ile Pro Val
             35                    40                    45

Pro Lys Pro Lys Pro Thr Glu Ile Leu Ile Asn Val Lys Tyr Ser Gly
50                     55                    60

Val Cys His Thr Asp Leu His Ala Trp Lys Gly Asp Trp Pro Leu Pro
65                70                    75                    80

Ala Lys Leu Pro Leu Val Gly Gly His Glu Gly Ala Gly Ile Val Val
                 85                    90                    95

Ala Lys Gly Ser Ala Val Thr Asn Phe Glu Ile Gly Asp Tyr Ala Gly
                100                   105                  110

Ile Lys Trp Leu Asn Gly Ser Cys Met Ser Cys Glu Phe Cys Glu Gln
           115                    120                   125

```
Gly Asp Glu Ser Asn Cys Glu His Ala Asp Leu Ser Gly Tyr Thr His
            130                 135                 140

Asp Gly Ser Phe Gln Gln Tyr Ala Thr Ala Asp Ala Ile Gln Ala Ala
145                 150                 155                 160

Lys Ile Pro Lys Gly Thr Asp Leu Ser Glu Val Ala Pro Ile Leu Cys
                165                 170                 175

Ala Gly Val Thr Val Tyr Lys Ala Leu Lys Thr Ala Asp Leu Arg Ala
            180                 185                 190

Gly Gln Trp Val Ala Ile Ser Gly Ala Ala Gly Gly Leu Gly Ser Leu
        195                 200                 205

Ala Val Gln Tyr Ala Lys Ala Met Gly Leu Arg Val Leu Gly Ile Asp
    210                 215                 220

Gly Gly Glu Gly Lys Lys Glu Leu Phe Glu Gln Cys Gly Gly Asp Val
225                 230                 235                 240

Phe Ile Asp Phe Thr Arg Tyr Pro Arg Asp Ala Pro Glu Lys Met Val
                245                 250                 255

Ala Asp Ile Lys Ala Ala Thr Asn Gly Leu Gly Pro His Gly Val Ile
            260                 265                 270

Asn Val Ser Val Ser Pro Ala Ala Ile Ser Gln Ser Cys Asp Tyr Val
        275                 280                 285

Arg Ala Thr Gly Lys Val Val Leu Val Gly Met Pro Ser Gly Ala Val
    290                 295                 300

Cys Lys Ser Asp Val Phe Thr His Val Val Lys Ser Leu Gln Ile Lys
305                 310                 315                 320

Gly Ser Tyr Val Gly Asn Arg Ala Asp Thr Arg Glu Ala Leu Glu Phe
                325                 330                 335

Phe Asn Glu Gly Lys Val Arg Ser Pro Ile Lys Val Val Pro Leu Ser
            340                 345                 350

Thr Leu Pro Glu Ile Tyr Glu Leu Met Glu Gln Gly Lys Ile Leu Gly
        355                 360                 365

Arg Tyr Val Val Asp Thr Ser Lys
    370                 375

<210> SEQ ID NO 3
<211> LENGTH: 3134
<212> TYPE: DNA
<213> ORGANISM: Issatchenkia orientalis
<220> FEATURE:
<221> NAME/KEY: CDS
<222> LOCATION: (1001)..(2134)

<400> SEQUENCE: 3
atgtatttgg agatttcgaa aagagtttgt atagagtctg taattgggtg tgtatttcaa      60
gacccacttt aaactgcgcc attaggagag ggagaggggg ggggggggg ggaagacggt     120 gaagtgtata caggatcgaa gaatagaagt tgtgtgtgtg ttttattacc cgtttcgatg    180
ggattcccag aagtggatac tatactgtct gcaatgcact acactctaaa aaagtattat    240
acattaccat acattagcaa atcaccaata ctctgcactg tttcagtgtg tgcacattgc    300
tacccaattg ggaaattgca gggaaaatga gaccccccct ccattccgta ttacgtaaga    360
caatatcagg gctgccgaat tcggcagaaa agccgagccg gccgagtcct cttgcacgga    420
gtgtgtccga aagggcagc tctgcagtgg gggagaggag gtcgcacgtc tatgcggtgt     480
tggcatggcc tgtgcgtgta cctgtcccct ccctgggcat cccccactgc gcgccttctc    540
cattgggcgc tgcgggcact ccgcgccgtt aatacaggag ggggggggg aaagcttaag     600
```

```
attagagcgg gtacagtcag tgggtgtatt gaccccattt ctgtcagtat aaaccccccg    660
ttgagccgcc ggtttggttg tttatggata aaatttttt tccccgcatg gagaagattg    720
agggggagaa ggaatgggaa aaaggccaga gccatctcca cagcggaatc cgaccgttaa    780
tggggtgaaa caccccccacc aggtagagca ggaagaatgg ggaaacaagg tggagagatg    840
gtcattgttg ggaatagtgg gaaaatgagg gggaagagaa tgactataaa atgggaaggg    900
ggtccaagtt atccaagcag tccatttaga aagggaaaaa taaagctata gatagaaacc    960
aaccaaacaa ccaaacaatt aaacaaacaa ttaaacgaac atg tta tcc aag acc     1015
                                            Met Leu Ser Lys Thr
                                            1             5 atc act gct gca ttg agg ggc aat aca act cgt act gca ttc aga atc     1063
Ile Thr Ala Ala Leu Arg Gly Asn Thr Thr Arg Thr Ala Phe Arg Ile
         10                 15                  20 aat gcc att aga agt tta gcg atc cca gct att cca gag aca caa aag     1111
Asn Ala Ile Arg Ser Leu Ala Ile Pro Ala Ile Pro Glu Thr Gln Lys
             25                  30                  35 ggt gtt atc ttt tat gag aac gga ggt gaa cta ttt tac aag gac att     1159
Gly Val Ile Phe Tyr Glu Asn Gly Gly Glu Leu Phe Tyr Lys Asp Ile
         40                  45                  50 cca gtt cca aag cca aag cca aat gag att ttg gtg aat gtc aag tat     1207
Pro Val Pro Lys Pro Lys Pro Asn Glu Ile Leu Val Asn Val Lys Tyr
55                  60                  65 tct ggt gtt tgt cat acc gat tta cac gca tgg aaa ggt gac tgg cct     1255
Ser Gly Val Cys His Thr Asp Leu His Ala Trp Lys Gly Asp Trp Pro
70                  75                  80                  85 ttg gcg acc aag ttg cca ttg gtt ggt gga cat gaa ggt gcc gga gtt     1303
Leu Ala Thr Lys Leu Pro Leu Val Gly Gly His Glu Gly Ala Gly Val
             90                  95                 100 gtt gtt gct aag ggg gac aat gtc acc aac ttt gaa att ggc gat tat     1351
Val Val Ala Lys Gly Asp Asn Val Thr Asn Phe Glu Ile Gly Asp Tyr
            105                 110                 115 gcc ggt atc aag tgg ttg aat ggt tca tgt atg ggg tgt gaa ttt tgc     1399
Ala Gly Ile Lys Trp Leu Asn Gly Ser Cys Met Gly Cys Glu Phe Cys
        120                 125                 130 caa caa ggt gca gag cca aac tgt cca cag gcc gac ttg agt ggt tac     1447
Gln Gln Gly Ala Glu Pro Asn Cys Pro Gln Ala Asp Leu Ser Gly Tyr
    135                 140                 145 acc cat gac ggg tcc ttt caa caa tat gcc act gcc gat gct gtt cag     1495
Thr His Asp Gly Ser Phe Gln Gln Tyr Ala Thr Ala Asp Ala Val Gln
150                 155                 160                 165 gca gcc aag att cct cag ggc act gat ttg gct caa gtt gcg cca att     1543
Ala Ala Lys Ile Pro Gln Gly Thr Asp Leu Ala Gln Val Ala Pro Ile
                170                 175                 180 tta tgt gca ggt att act gtc tat aag gct tta aag act gca gaa tta     1591
Leu Cys Ala Gly Ile Thr Val Tyr Lys Ala Leu Lys Thr Ala Glu Leu
            185                 190                 195 aga cca ggt caa tgg gtt gcc att tct ggt gct gct gga ggt tta ggt     1639
Arg Pro Gly Gln Trp Val Ala Ile Ser Gly Ala Ala Gly Gly Leu Gly
        200                 205                 210 tct ctt gct gtt caa tat gcc aag gcc atg ggt ttg aga gtt ttg ggt     1687
Ser Leu Ala Val Gln Tyr Ala Lys Ala Met Gly Leu Arg Val Leu Gly
    215                 220                 225 att gat ggt ggt gag gag aag ggc aag ttt gca aag tct ctt gga gct     1735
Ile Asp Gly Gly Glu Glu Lys Gly Lys Phe Ala Lys Ser Leu Gly Ala
230                 235                 240                 245 gaa gtt ttc att gat ttc acc aaa tcc aag gac att gtc aag gat atc     1783
Glu Val Phe Ile Asp Phe Thr Lys Ser Lys Asp Ile Val Lys Asp Ile
                250                 255                 260
```

-continued

```
caa gag gcc acc aat ggt ggt cca cat ggt gtc att aat gtt tct gtt      1831
Gln Glu Ala Thr Asn Gly Gly Pro His Gly Val Ile Asn Val Ser Val
            265                 270                 275 tct cca gct gct att tct caa agt acc cag tat gtc aga acc ttg ggt      1879
Ser Pro Ala Ala Ile Ser Gln Ser Thr Gln Tyr Val Arg Thr Leu Gly
        280                 285                 290 aag gtt gtc ctt gtt gga tta cca gcg cat gct gta tgc gag tct tcg      1927
Lys Val Val Leu Val Gly Leu Pro Ala His Ala Val Cys Glu Ser Ser
    295                 300                 305 gtt ttc gac cat gtt gtc aag tcg att caa att aga ggc tct tat gtt      1975
Val Phe Asp His Val Val Lys Ser Ile Gln Ile Arg Gly Ser Tyr Val
310                 315                 320                 325 ggt aac agg gaa gat act agt gag gct att gat ttt ttc acc agg ggt      2023
Gly Asn Arg Glu Asp Thr Ser Glu Ala Ile Asp Phe Phe Thr Arg Gly
                330                 335                 340 tta gtg aag tca cca att aag att gtt ggt ttg agt gag ttg cca aag      2071
Leu Val Lys Ser Pro Ile Lys Ile Val Gly Leu Ser Glu Leu Pro Lys
            345                 350                 355 atc tat gaa ttg atg gag caa ggt aag att tta ggc aga tat gtt gtt      2119
Ile Tyr Glu Leu Met Glu Gln Gly Lys Ile Leu Gly Arg Tyr Val Val
        360                 365                 370 gac act tcg aaa tga tgggctgact tggtgtact ggtgtgacgt ttttatgtgt       2174
Asp Thr Ser Lys
        375 atattgatat gcatggggga tgtatagtga tgaggagtag agtatataac gaaatgaaat    2234 gaaataatat gatatgataa gataagatga gatcaaatac gataatataa gatgcgacat    2294 gaggagttca atgtagcata ctacacgatg ctgcagtaca actctgatac gctagactat    2354 actatacaaa actgtagtac actatacgtt agtgtagtat ccagaaacaa cactgcttta    2414 tagtacaata caactctata atactatagt atactatgcc aaaccacgta ataccataat    2474 atgctccacg acatggtaca atgtgctata cttcatacta ttataccata tatactccga    2534 tatattattg atatactatt ttatactata ataccatacc acacaacact acattacaac    2594 gagcaacctt accataaatg tcagttatgt ggcccggaga ctctctcgag gagcgtgttc    2654 acctcgttgt agacgttctg cacatcctct ccgagcaggg cacgtgctcc catagtggga    2714 ggggcctctt ccaagggcga cccgcggcgc cccgcaccaa gaagcgcctg ttccttgagc    2774 gcatgtgcaa tattgagaag ggtgtctatg ctgcgaagaa cggtgtctgt gtcggcagca    2834 gcagcagcgg cgtctgctcc ctgggcggaa cgtgtcttcc ccgctaaggg gagcacagca    2894 agaatatcat gtaatgcagc aagagcattc tgagttgaag tatcgatttt cgatgccata    2954 ttgtatgtgt attgtattaa gtgtgtattg tcttaagtgt gtaagagaca tttatttgtg    3014 tcaacaatag cgacgccact gaaaacctca aatatcgtat ttattaatcc ccttccccc     3074 agcgcagatc gtcccgtcga tttctattgt ttgggcatta tcagcgacgc gacggcgacg    3134
```

<210> SEQ ID NO 4
<211> LENGTH: 377
<212> TYPE: PRT
<213> ORGANISM: Issatchenkia orientalis

<400> SEQUENCE: 4

```
Met Leu Ser Lys Thr Ile Thr Ala Ala Leu Arg Gly Asn Thr Thr Arg
1               5                   10                  15

Thr Ala Phe Arg Ile Asn Ala Ile Arg Ser Leu Ala Ile Pro Ala Ile
            20                  25                  30
```

```
Pro Glu Thr Gln Lys Gly Val Ile Phe Tyr Glu Asn Gly Glu Leu
        35                  40                  45

Phe Tyr Lys Asp Ile Pro Val Pro Lys Pro Lys Pro Asn Glu Ile Leu
 50                  55                  60

Val Asn Val Lys Tyr Ser Gly Val Cys His Thr Asp Leu His Ala Trp
 65                  70                  75                  80

Lys Gly Asp Trp Pro Leu Ala Thr Lys Leu Pro Leu Val Gly His
                85                  90                  95

Glu Gly Ala Gly Val Val Ala Lys Gly Asp Asn Val Thr Asn Phe
                100                 105                 110

Glu Ile Gly Asp Tyr Ala Gly Ile Lys Trp Leu Asn Gly Ser Cys Met
                115                 120                 125

Gly Cys Glu Phe Cys Gln Gln Gly Ala Glu Pro Asn Cys Pro Gln Ala
        130                 135                 140

Asp Leu Ser Gly Tyr Thr His Asp Gly Ser Phe Gln Gln Tyr Ala Thr
145                 150                 155                 160

Ala Asp Ala Val Gln Ala Ala Lys Ile Pro Gln Gly Thr Asp Leu Ala
                165                 170                 175

Gln Val Ala Pro Ile Leu Cys Ala Gly Ile Thr Val Tyr Lys Ala Leu
                180                 185                 190

Lys Thr Ala Glu Leu Arg Pro Gly Gln Trp Val Ala Ile Ser Gly Ala
                195                 200                 205

Ala Gly Gly Leu Gly Ser Leu Ala Val Gln Tyr Ala Lys Ala Met Gly
                210                 215                 220

Leu Arg Val Leu Gly Ile Asp Gly Gly Glu Glu Lys Gly Lys Phe Ala
225                 230                 235                 240

Lys Ser Leu Gly Ala Glu Val Phe Ile Asp Phe Thr Lys Ser Lys Asp
                245                 250                 255

Ile Val Lys Asp Ile Gln Glu Ala Thr Asn Gly Gly Pro His Gly Val
                260                 265                 270

Ile Asn Val Ser Val Ser Pro Ala Ala Ile Ser Gln Ser Thr Gln Tyr
                275                 280                 285

Val Arg Thr Leu Gly Lys Val Val Leu Val Gly Leu Pro Ala His Ala
                290                 295                 300

Val Cys Glu Ser Ser Val Phe Asp His Val Lys Ser Ile Gln Ile
305                 310                 315                 320

Arg Gly Ser Tyr Val Gly Asn Arg Glu Asp Thr Ser Glu Ala Ile Asp
                325                 330                 335

Phe Phe Thr Arg Gly Leu Val Lys Ser Pro Ile Lys Ile Val Gly Leu
                340                 345                 350

Ser Glu Leu Pro Lys Ile Tyr Glu Leu Met Glu Gln Gly Lys Ile Leu
                355                 360                 365

Gly Arg Tyr Val Val Asp Thr Ser Lys
                370                 375

<210> SEQ ID NO 5
<211> LENGTH: 1053
<212> TYPE: DNA
<213> ORGANISM: Issatchenkia orientalis
<220> FEATURE:
<221> NAME/KEY: CDS
<222> LOCATION: (1)..(1053)

<400> SEQUENCE: 5 atg tct tac gaa atc cca caa aca caa aag gcc tgt gtc ttt tac gaa       48
Met Ser Tyr Glu Ile Pro Gln Thr Gln Lys Ala Cys Val Phe Tyr Glu
```

-continued

| | | | | | | | | | | | | | | | | |
|---|---|---|---|---|---|---|---|---|---|---|---|---|---|---|---|---|
| 1 | | | | 5 | | | | | 10 | | | | | 15 | | |

```
aac ggc ggc cca atc aca tac aag gac att cca gtt cca aag cca aaa    96
Asn Gly Gly Pro Ile Thr Tyr Lys Asp Ile Pro Val Pro Lys Pro Lys
            20                  25                  30 cct act gag att tta gtc aag gtt ctg tac tct ggt gtc tgc cac acc   144
Pro Thr Glu Ile Leu Val Lys Val Leu Tyr Ser Gly Val Cys His Thr
                35                  40                  45 gac ttg cac gca tgg aag ggt gac tgg cct cta gct acc aag ttg cca   192
Asp Leu His Ala Trp Lys Gly Asp Trp Pro Leu Ala Thr Lys Leu Pro
    50                  55                  60 ttg gtt ggt ggt cac gaa ggt gcc ggt gtt gtt gtt gcc aag ggt gaa   240
Leu Val Gly Gly His Glu Gly Ala Gly Val Val Val Ala Lys Gly Glu
65                  70                  75                  80 aac gtc acc tct ttt gag att ggt gat tac gca ggt atc aag tgg ttg   288
Asn Val Thr Ser Phe Glu Ile Gly Asp Tyr Ala Gly Ile Lys Trp Leu
                85                  90                  95 aat ggt tca tgt atg ggt tgt gaa ttc tgt gaa caa ggt gct gaa cca   336
Asn Gly Ser Cys Met Gly Cys Glu Phe Cys Glu Gln Gly Ala Glu Pro
            100                 105                 110 aac tgt cct aag gcc gac ttg agt ggt tac acc cac gac ggt tcc ttc   384
Asn Cys Pro Lys Ala Asp Leu Ser Gly Tyr Thr His Asp Gly Ser Phe
        115                 120                 125 caa cag tat gct act gct gac gct att caa gct gca cac atc tcc aag   432
Gln Gln Tyr Ala Thr Ala Asp Ala Ile Gln Ala Ala His Ile Ser Lys
    130                 135                 140 gaa acc gac ttg gct ggt gtt gct cca atc ttg tgt gca ggt gtc act   480
Glu Thr Asp Leu Ala Gly Val Ala Pro Ile Leu Cys Ala Gly Val Thr
145                 150                 155                 160 gtc tac aag gct tta aag act gca gac ctt aga gca ggt gaa tgg gtt   528
Val Tyr Lys Ala Leu Lys Thr Ala Asp Leu Arg Ala Gly Glu Trp Val
                165                 170                 175 tgt att tcc ggt gca gct ggt ggt tta ggt tct ctt gct att caa tat   576
Cys Ile Ser Gly Ala Ala Gly Gly Leu Gly Ser Leu Ala Ile Gln Tyr
            180                 185                 190 gca aag gct atg ggt ctg aga gtt gtt ggt att gac ggt ggt gac gaa   624
Ala Lys Ala Met Gly Leu Arg Val Val Gly Ile Asp Gly Gly Asp Glu
        195                 200                 205 aag aag gaa ttg tgt aaa tcc ctt ggt gct gaa gca ttt att gat ttc   672
Lys Lys Glu Leu Cys Lys Ser Leu Gly Ala Glu Ala Phe Ile Asp Phe
    210                 215                 220 aca aag acc aag gat atc gtc aag gct gtc caa gag gca acc aat ggt   720
Thr Lys Thr Lys Asp Ile Val Lys Ala Val Gln Glu Ala Thr Asn Gly
225                 230                 235                 240 ggt cca cat ggt gtc atc aat gtc tct gtc tct gaa gct gca att tct   768
Gly Pro His Gly Val Ile Asn Val Ser Val Ser Glu Ala Ala Ile Ser
                245                 250                 255 caa tct tgt gaa tac gtt aga cct cta ggt aag gtt gtt ctt gtt ggt   816
Gln Ser Cys Glu Tyr Val Arg Pro Leu Gly Lys Val Val Leu Val Gly
            260                 265                 270 tta cca gca ggc gca caa gtc aaa act ggt gtc ttt gaa gcc gtt gtc   864
Leu Pro Ala Gly Ala Gln Val Lys Thr Gly Val Phe Glu Ala Val Val
        275                 280                 285 aag tct att gaa att aag ggt tct tat gtc ggt aac aga aag gat acc   912
Lys Ser Ile Glu Ile Lys Gly Ser Tyr Val Gly Asn Arg Lys Asp Thr
    290                 295                 300 gcc gaa gca ctt gac ttc tac act aga ggc ttg gtc aag tct cca ttc   960
Ala Glu Ala Leu Asp Phe Tyr Thr Arg Gly Leu Val Lys Ser Pro Phe
305                 310                 315                 320 aag att gtc ggt tta tcc gaa ttg cca aaa gtc ttt gaa ctc atg gaa  1008
```

```
Lys Ile Val Gly Leu Ser Glu Leu Pro Lys Val Phe Glu Leu Met Glu
                325                 330                 335 cag ggt aag att tta ggt aga atg gtc tta gac acc tcc aaa taa       1053
Gln Gly Lys Ile Leu Gly Arg Met Val Leu Asp Thr Ser Lys
            340                 345                 350
```

<210> SEQ ID NO 6
<211> LENGTH: 350
<212> TYPE: PRT
<213> ORGANISM: Issatchenkia orientalis

<400> SEQUENCE: 6

```
Met Ser Tyr Glu Ile Pro Gln Thr Gln Lys Ala Cys Val Phe Tyr Glu
1               5                   10                  15

Asn Gly Gly Pro Ile Thr Tyr Lys Asp Ile Pro Val Pro Lys Pro Lys
            20                  25                  30

Pro Thr Glu Ile Leu Val Lys Val Leu Tyr Ser Gly Val Cys His Thr
        35                  40                  45

Asp Leu His Ala Trp Lys Gly Asp Trp Pro Leu Ala Thr Lys Leu Pro
    50                  55                  60

Leu Val Gly Gly His Glu Gly Ala Gly Val Val Ala Lys Gly Glu
65                  70                  75                  80

Asn Val Thr Ser Phe Glu Ile Gly Asp Tyr Ala Gly Ile Lys Trp Leu
                85                  90                  95

Asn Gly Ser Cys Met Gly Cys Glu Phe Cys Glu Gln Gly Ala Glu Pro
            100                 105                 110

Asn Cys Pro Lys Ala Asp Leu Ser Gly Tyr Thr His Asp Gly Ser Phe
        115                 120                 125

Gln Gln Tyr Ala Thr Ala Asp Ala Ile Gln Ala Ala His Ile Ser Lys
    130                 135                 140

Glu Thr Asp Leu Ala Gly Val Ala Pro Ile Leu Cys Ala Gly Val Thr
145                 150                 155                 160

Val Tyr Lys Ala Leu Lys Thr Ala Asp Leu Arg Ala Gly Glu Trp Val
                165                 170                 175

Cys Ile Ser Gly Ala Ala Gly Gly Leu Gly Ser Leu Ala Ile Gln Tyr
            180                 185                 190

Ala Lys Ala Met Gly Leu Arg Val Val Gly Ile Asp Gly Gly Asp Glu
        195                 200                 205

Lys Lys Glu Leu Cys Lys Ser Leu Gly Ala Glu Ala Phe Ile Asp Phe
    210                 215                 220

Thr Lys Thr Lys Asp Ile Val Lys Ala Val Gln Glu Ala Thr Asn Gly
225                 230                 235                 240

Gly Pro His Gly Val Ile Asn Val Ser Val Ser Glu Ala Ala Ile Ser
                245                 250                 255

Gln Ser Cys Glu Tyr Val Arg Pro Leu Gly Lys Val Val Leu Val Gly
            260                 265                 270

Leu Pro Ala Gly Ala Gln Val Lys Thr Gly Val Phe Glu Ala Val Val
        275                 280                 285

Lys Ser Ile Glu Ile Lys Gly Ser Tyr Val Gly Asn Arg Lys Asp Thr
    290                 295                 300

Ala Glu Ala Leu Asp Phe Tyr Thr Arg Gly Leu Val Lys Ser Pro Phe
305                 310                 315                 320

Lys Ile Val Gly Leu Ser Glu Leu Pro Lys Val Phe Glu Leu Met Glu
                325                 330                 335

Gln Gly Lys Ile Leu Gly Arg Met Val Leu Asp Thr Ser Lys
            340                 345                 350
```

-continued

```
                340             345             350
```

<210> SEQ ID NO 7
<211> LENGTH: 23
<212> TYPE: DNA
<213> ORGANISM: Artificial Sequence
<220> FEATURE:
<223> OTHER INFORMATION: PCR primer

<400> SEQUENCE: 7
cttgtgaata cgttagacct cta                                              23

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
gagacttgac caagcctcta                                                  20

<210> SEQ ID NO 9
<211> LENGTH: 23
<212> TYPE: DNA
<213> ORGANISM: Artificial Sequence
<220> FEATURE:
<223> OTHER INFORMATION: PCR primer

<400> SEQUENCE: 9
catgtgacta tgttagagca act                                              23

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
ggagatctga ccttaccttc a                                                21

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
cccagtatgt cagaaccttg                                                  20

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
gtgacttcac taaacccctg                                                  20

<210> SEQ ID NO 13
<211> LENGTH: 348
<212> TYPE: PRT
<213> ORGANISM: Saccharomyces cerevisiae

<400> SEQUENCE: 13

```
Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345
```

<210> SEQ ID NO 14
<211> LENGTH: 348
<212> TYPE: PRT
<213> ORGANISM: Saccharomyces cerevisiae

<400> SEQUENCE: 14

```
Met Ser Ile Pro Glu Thr Gln Lys Ala Ile Ile Phe Tyr Glu Ser Asn
1               5                   10                  15
```

Gly Lys Leu Glu His Lys Asp Ile Pro Val Pro Lys Pro Lys Pro Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125

Tyr Ala Thr Ala Asp Ala Val Gln Ala Ala His Ile Pro Gln Gly Thr
    130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
        195                 200                 205

Glu Leu Phe Thr Ser Leu Gly Gly Glu Val Phe Ile Asp Phe Thr Lys
    210                 215                 220

Glu Lys Asp Ile Val Ser Ala Val Val Lys Ala Thr Asn Gly Gly Ala
225                 230                 235                 240

His Gly Ile Ile Asn Val Ser Val Ser Glu Ala Ala Ile Glu Ala Ser
                245                 250                 255

Thr Arg Tyr Cys Arg Ala Asn Gly Thr Val Val Leu Val Gly Leu Pro
            260                 265                 270

Ala Gly Ala Lys Cys Ser Ser Asp Val Phe Asn His Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
                325                 330                 335

Gln Ile Ala Gly Arg Tyr Val Val Asp Thr Ser Lys
            340                 345

<210> SEQ ID NO 15
<211> LENGTH: 375
<212> TYPE: PRT
<213> ORGANISM: Saccharomyces cerevisiae

<400> SEQUENCE: 15

Met Leu Arg Thr Ser Thr Leu Phe Thr Arg Arg Val Gln Pro Ser Leu
1               5                   10                  15

Phe Ser Arg Asn Ile Leu Arg Leu Gln Ser Thr Ala Ala Ile Pro Lys
            20                  25                  30

-continued

```
Thr Gln Lys Gly Val Ile Phe Tyr Glu Asn Lys Gly Lys Leu His Tyr
     35                  40                  45
Lys Asp Ile Pro Val Pro Glu Pro Lys Pro Asn Glu Ile Leu Ile Asn
 50                  55                  60
Val Lys Tyr Ser Gly Val Cys His Thr Asp Leu His Ala Trp His Gly
 65                  70                  75                  80
Asp Trp Pro Leu Pro Val Lys Leu Pro Leu Val Gly Gly His Glu Gly
             85                  90                  95
Ala Gly Val Val Val Lys Leu Gly Ser Asn Val Lys Gly Trp Lys Val
             100                 105                 110
Gly Asp Leu Ala Gly Ile Lys Trp Leu Asn Gly Ser Cys Met Thr Cys
         115                 120                 125
Glu Phe Cys Glu Ser Gly His Glu Ser Asn Cys Pro Asp Ala Asp Leu
     130                 135                 140
Ser Gly Tyr Thr His Asp Gly Ser Phe Gln Gln Phe Ala Thr Ala Asp
 145                 150                 155                 160
Ala Ile Gln Ala Ala Lys Ile Gln Gln Gly Thr Asp Leu Ala Glu Val
             165                 170                 175
Ala Pro Ile Leu Cys Ala Gly Val Thr Val Tyr Lys Ala Leu Lys Glu
             180                 185                 190
Ala Asp Leu Lys Ala Gly Asp Trp Val Ala Ile Ser Gly Ala Ala Gly
         195                 200                 205
Gly Leu Gly Ser Leu Ala Val Gln Tyr Ala Thr Ala Met Gly Tyr Arg
     210                 215                 220
Val Leu Gly Ile Asp Ala Gly Glu Glu Lys Glu Lys Leu Phe Lys Lys
 225                 230                 235                 240
Leu Gly Gly Glu Val Phe Ile Asp Phe Thr Lys Thr Lys Asn Met Val
             245                 250                 255
Ser Asp Ile Gln Glu Ala Thr Lys Gly Gly Pro His Gly Val Ile Asn
             260                 265                 270
Val Ser Val Ser Glu Ala Ala Ile Ser Leu Ser Thr Glu Tyr Val Arg
         275                 280                 285
Pro Cys Gly Thr Val Val Leu Val Gly Leu Pro Ala Asn Ala Tyr Val
     290                 295                 300
Lys Ser Glu Val Phe Ser His Val Val Lys Ser Ile Asn Ile Lys Gly
 305                 310                 315                 320
Ser Tyr Val Gly Asn Arg Ala Asp Thr Arg Glu Ala Leu Asp Phe Phe
             325                 330                 335
Ser Arg Gly Leu Ile Lys Ser Pro Ile Lys Ile Val Gly Leu Ser Glu
             340                 345                 350
Leu Pro Lys Val Tyr Asp Leu Met Glu Lys Gly Lys Ile Leu Gly Arg
         355                 360                 365
Tyr Val Val Asp Thr Ser Lys
     370                 375
```